(12) United States Patent
Zendejas Hernandez et al.

(10) Patent No.: US 11,931,372 B2
(45) Date of Patent: Mar. 19, 2024

(54) PHARMACEUTICAL COMPOSITION CONTAINING PENTACYCLIC TRITERPENOIDS

(71) Applicant: SPV TIMSER, S.A.P.I. DE C.V., Mexico City (MX)

(72) Inventors: Ulises Zendejas Hernandez, Ixtapaluca (MX); Alicia Teresa Smith Ogarrio, Mexico City (MX); Mercedes Gutiérrez Smith, Mexico City (MX)

(73) Assignee: SPV TIMSER, S.A.P.I. DE C.V., Mexico City (MX)

( * ) Notice: Subject to any disclaimer, the term of this patent is extended or adjusted under 35 U.S.C. 154(b) by 0 days.

(21) Appl. No.: 17/923,776

(22) PCT Filed: Mar. 25, 2022

(86) PCT No.: PCT/MX2022/050031
§ 371 (c)(1),
(2) Date: Nov. 7, 2022

(87) PCT Pub. No.: WO2022/235146
PCT Pub. Date: Nov. 10, 2022

(65) Prior Publication Data
US 2023/0210876 A1    Jul. 6, 2023

(30) Foreign Application Priority Data
May 4, 2021    (MX) .................... MX/a/2021/005280

(51) Int. Cl.
| | | |
|---|---|---|
| *A61K 31/704* | (2006.01) | |
| *A61K 31/19* | (2006.01) | |
| *A61K 47/10* | (2017.01) | |
| *A61K 47/26* | (2006.01) | |
| *A61P 31/12* | (2006.01) | |

(52) U.S. Cl.
CPC ............ *A61K 31/704* (2013.01); *A61K 31/19* (2013.01); *A61K 47/10* (2013.01); *A61K 47/26* (2013.01); *A61P 31/12* (2018.01)

(58) Field of Classification Search
None
See application file for complete search history.

(56) References Cited

U.S. PATENT DOCUMENTS

| | | |
|---|---|---|
| 5,186,945 A | 2/1993 | Shanbrom |
| 6,329,339 B1 | 12/2001 | Pompei et al. |
| 2011/0311592 A1* | 12/2011 | Birbara .................. A61K 8/498 424/59 |
| 2012/0053141 A1 | 3/2012 | Zhang et al. |

FOREIGN PATENT DOCUMENTS

CN    110585122 B    3/2021

OTHER PUBLICATIONS

Hu et al. CN 110585122 A, 2019, machine translation (Year: 2019).*

* cited by examiner

*Primary Examiner* — Dale R Miller
(74) *Attorney, Agent, or Firm* — Volpe Koenig

(57) ABSTRACT

This invention refers to pharmaceutical compositions containing synergistic combinations of pentacyclic triterpenoids as active principles and denotes that some specific combinations between these types of drugs exhibit effects for the prevention or inhibition of viral infections. The compositions are found in specific quantities and proportions that enhance the pharmacological properties of the compounds, improving their bioavailability and pharmacokinetic properties, while reducing their toxicological and irritability effects, especially in the respiratory tract and the lungs.

15 Claims, 19 Drawing Sheets

PHARMACEUTICAL COMPOSITION CONTAINING PENTACYCLIC TRITERPENOIDS

CROSS REFERENCE TO RELATED APPLICATIONS

This application is a 35 U.S.C. § 371 national stage of International Application No. PCT/MX2022/050031, which was filed Mar. 25, 2022, and claims the benefit of MX Patent Application No. MX/a/2021/005280, filed May 4, 2021, both of which are incorporated herein by reference as if fully set forth.

INDUSTRIAL PROPERTY RIGHTS RESERVED

Part of the description herein contains material subject to industrial property right protection. The rights owner expresses no objection to the reproduction of the patent document or application description via facsimile by any person, as stated in the patent file or records at the Patents and Trademarks Office. However, all other industrial property rights shall remain reserved.

FIELD OF INVENTION

This invention is related to pharmaceutical compositions containing pentacyclic triterpenoids as active components, especially glycyrrhizic acid and 18-β-glycyrrhetinic acid. Said compositions are characterized by being in combination with pharmaceutically acceptable excipients and being adapted to be administrable in humans. These compositions are suitable to be administrable by the oral, nasal, cutaneous, intravenous injectable or inhaled routes, and to be used in the treatment of respiratory diseases and especially viral infectious diseases. These formulations are especially effective for the prevention, treatment, and post-treatment of respiratory infections, particularly those whose transmission is through the mechanism of interaction with angiotensin-converting enzyme 2, ACE2, such as the severe acute respiratory syndrome coronavirus, SARS-CoV, and its type 2, SARS-CoV2.

It is important to note that there are several references related to pentacyclic triterpenoids and, specifically, to the glycyrrhizic acid (also referred to as GA) and 18-β glycyrrhetinic acid (also referred to as enoxolone or EN) components. These references indicate different common names for each of said components. In this document, these components correspond to the following structures:

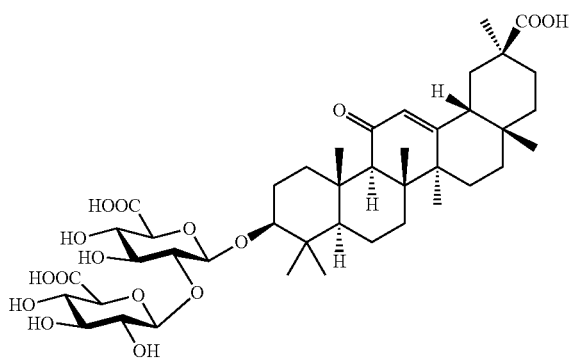

Glycyrrhizic Acid, (GA)

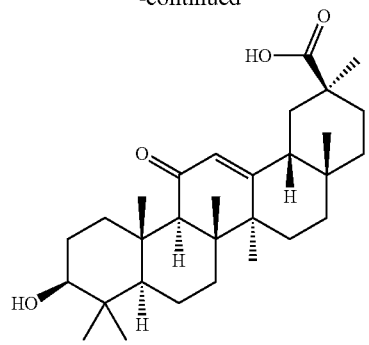

18-β Glycyrrhetinic Acid, (EN)

BRIEF DESCRIPTION OF THE INVENTION

This invention refers to pharmaceutical compositions containing combinations of pentacyclic triterpenoids as active components and denotes that some specific combinations between these types of drugs result in surprising effects for the prevention or inhibition of viral and/or respiratory infections. The compositions are found in specific quantities and proportions that enhance the pharmacological properties of the compounds, thus improving their bioavailability and pharmacokinetic properties, while reducing their toxicological and irritability effects, especially in the respiratory tract and the lungs.

The compositions described herein are adapted to be administrable by intravenous, cutaneous, oral, nasal, or inhalation route to humans. The compositions can be applied by one or more of these routes to improve the bioavailability of their active ingredients and achieve a high local concentration in the respiratory tract (nasal cavities, pharynx, larynx, trachea, bronchi, and bronchioles) and the lungs, which are especially vulnerable to infection by viral agents.

The different antiviral, antioxidant, antibacterial, analgesic, anti-inflammatory, regenerative and immunomodulatory properties of the active ingredients used in this composition act together to combat respiratory tract infections, reduce the severity of any associated symptoms, and reduce and relieve post-infection effects. The combination of the pharmacological properties of this invention makes the compositions especially useful to be used in the prevention, treatment and recovery of patients suffering or who have suffered viral infections, especially those infections caused by contagion with virus interaction with angiotensin-converting enzyme 2, (ACE2).

Among the preferred pentacyclic triterpenoids is the 18-β glycyrrhetinic acid (EN), classified as Class II in the Biopharmaceutics Classification System, presenting low polarity, high hydrophobicity, and moderate permeability. Hence, the limiting step for absorption into the human bloodstream is the dissolution of the drug, which is then absorbed and distributed to different organs or to the target site.

Another preferred pentacyclic triterpenoid is glycyrrhizic acid (GA), which, despite being soluble in water, exhibits reduced permeability (Class III in the Biopharmaceutics Classification System). Hence, its absorption is in function of the excipients and manufacturing processes.

On the other hand, the selection of excipients and pharmaceutical forms define the absorption of the drug and thus the potentiation of the desired therapeutic effect. For the specific case of inhaled pharmaceutical forms, we can mention that these forms are used when the site of action is focused on the upper airways (nasal cavity, throat, mouth, and larynx) and lower airways (trachea, bronchi, bronchioles, and lungs), and wherein the pharmaceutical form administered does not necessarily require absorption, since the largest proportion of the drug has been in contact with the site of action. In addition, the absorption of the drug will promote a homogeneous distribution in the target organ and in the circulatory system, which boosters the therapeutic effects of the drug administered. Likewise, this absorption can be conducted both in the airways and in the gastrointestinal tract, thereby absorbing the portion that remained unabsorbed in the upper airways and which is generated by the intake of liquids or food.

The promotion of the drug absorption at the site of action enhances its therapeutic effect and it is estimated to reduce the systemic effects caused by the disease being treated (collateral damage). For the specific case of EN, in addition to its antiviral effectiveness, its absorption and distribution can promote effects such as: anti-inflammatory, antioxidant, antimicrobial, immunomodulatory, re-epithelializing, and antifibrotic effects, in addition to having the ability to cross the blood-brain barrier.

BACKGROUND

Respiratory tract infections are one of the most frequent diseases that affect all population groups at a global scale. Although their origins may be due to several agents, the diseases caused by viral etiology are part of the technical field of this application. Viruses that commonly originate these diseases belong to the orthomyxoviridae, paramyxoviridae, picornaviridae, coronavirus, and adenovirus families.

As respiratory diseases exert a direct impact on health, quality of life and socioeconomic factors, there must be treatments and vaccines available for their management and prevention. Drugs commonly used to treat viral infections include adamantanes (amantadine and rimantadine), neuraminidase inhibitors (zanamivir and oseltamivir), ribavirin, cidofovir, and pleconaril, among others. The downside of these drugs is that they cause severe side effects, can be very expensive, or they can be obsolete to new viral variants. Other treatments for viral infections include the use of plasma from people convalescing from viral infections, monoclonal antibodies, antisense oligonucleotides, peptides, steroids, and interferons. Nevertheless, further studies are still required to validate the effectiveness and safety of these treatments.

Although in most viral infections, it is sufficient to administer one of the known known drugs, or through palliative treatments, the lack of antiviral drugs is especially critical in the face of the sudden emergence of viral strains with pandemic potential since containing epidemic outbreaks without effective treatments is a cumbersome task. As examples thereof, we may briefly point out the 1981 H1N1 influenza outbreak which caused between 40 and 100 million deaths. From 2002 to 2003, a new severe form of pneumonia caused by a coronavirus (SARS-CoV) surfaced, leaving 8,096 cases and 744 deaths in 29 countries across 5 continents. In 2009, a new A-H1N1 influenza variant caused a pandemic which reach an estimated toll of 100,000 to 400,000 deaths around the world. This denotes the periodical emergence of severe viral epidemics, whose impact depends on the virulence of the corresponding strain.

At the end of 2019, with the sudden appearance of the SARS-CoV2 coronavirus strain, more than 2,500,000 deaths were reported worldwide throughout 2020 and the first few months of 2021. Regarding this virus, 80% of all infected patients do not advance to a serious clinical prognosis, 20% experience severe symptoms, and between 3 and 10% may have a fatal outcome. In addition to the symptoms reported throughout the course of the infection, it has been observed that, in some cases, coronavirus patients experience post-infection effects such as tissue damage in organs such as the heart, lungs, the nervous system and the brain, mental health issues, chronic fatigue, blood clots, and/or circulatory system problems. Many of these long-term effects and impacts are still unknown.

As for specific examples, even when SARS-CoV2 mortality rates are relatively low, the virus exhibits high transmission rates. Hence, a large part of the population becomes infected simultaneously, thereby saturating and collapsing national health systems, leading to inadequate care, and increasing death tolls. In addition to this, the saturation of health systems causes the neglect of other diseases, a situation that increases their mortality. Within this context, finding pharmacological treatments for COVID 19, a disease caused by SARS-CoV2, has been a priority.

To combat COVID-19 disease, several known drugs have been used. For example, chloroquine, hydroxychloroquine, azithromycin, remdesivir, lopinavir-ritonavir, favipiravir, IL-6 pathway inhibitors, ivermectin, corticosteroids, convalescent plasma, heparin, vitamin C, among others, have all been tested as treatment options. Even when these drugs have been reported as helpful in some cases, none of them has been deemed as an effective treatment yet.

Technical Field Background

The root of *Glycyrrhiza uralensis* contains several compounds with pharmacological activity, including flavonoids, phenols with isoprenoid substitutions, isoflavonoids, saponins, and several volatile compounds. Among these compounds, triterpene saponins, mainly glycyrrhizic acid (GA) and 18-β glycyrrhetinic acid (EN), found in licorice as a mixture of their potassium and calcium salts, are of special interest. Glycyrrhizic acid (GA) and 18-β-glycyrrhetinic acid (EN) are pentacyclic triterpenoids of the oleanane type. These compounds have been identified as main bioactive compounds from *Glycyrrhiza uralensis* extract. In fact, various pharmacological properties have been attributed to these compounds.

Different studies report the use of pentacyclic triterpenoids as an alternative in the prevention, treatment, and post-treatment of infectious diseases of the respiratory system due to their distinct physicochemical and pharmacological characteristics.

In 2003, J. Cinatl et al. reported GA as an inhibitor of SARS-CoV as it prevented virus replication in culture cells.

Harald Murck (May 28, 2020) mentions that GA can function as a steric blocker of the ACE2 protein, which is the pathway for SARS-CoV2 entry into the cell. GA inhibits the expression of the TMPRSS2 protein, an important protein for viral infection and overall, this study determined that GA and its derivatives exhibit antiviral properties.

Luo Pan et al. (Apr. 29, 2020) describe the pharmacological perspectives of GA, highlighting its role as an immunoregulator of cytokines, as a promoter of interferons with antiviral activity, and as an inhibitor of the thrombin protein, which generates the blood clots associated with the disease.

U.S. Pat. No. 5,128,149A SHANBROM (Jul. 7, 1992) describes a treatment of mammalian cells and biological fluids with compounds referred in the documents glycyrrhizic compounds [ . . . ] to inactivate viruses and to improve the containers to provide such treatment. In addition, this document refers to the treatment of whole blood to inactivate or destroy infectious viruses found in animal fluids and cells, such as cytomegalovirus, which aggravates infections in blood transfusion recipients.

Document US2011052727A1 POLANSKY (Mar. 3, 2011) describes methods to prevent or treat an infection by an influenza virus. In a preferred embodiment, the methods include administering to a subject an effective dose of a nutritional supplement, wherein one of the components of the supplement is glycyrrhizic acid.

Given this background, there are several sources that indicate the use of GA for the treatment, prevention, and post-treatment of viral diseases. One of the problems with GA is the rapid metabolism it undergoes when administered orally or though injection to humans. For this reason, it has been suggested that oral or injected GA administration may not achieve the local concentrations required for a therapeutic effect. Likewise, the necessary concentrations to generate therapeutic antiviral effects are extremely high for the drug to be considered as completely useful. As will be seen later, other problems reported when GA or EN are applied separately in relatively high concentrations are irritability and toxicity.

Some references state that, a critical infection step is when the virus enters human host cells, which is enabled by the interaction between the SARS-CoV-2 Spike (S) protein on the surface of the viral particle and the angiotensin converting enzyme 2 (ACE2) on the surface of human cells.

The present invention overcomes these limitations by providing pharmaceutical compositions adapted to be administrable to a subject that comprising a synergistic combination of at least two pentacyclic triterpenoids, mainly by inhalation.

The invention is characterized by using optimal proportions with more than one pentacyclic triterpenoid, in combination with pharmaceutically acceptable excipients, to block the interaction between the Spike(S) protein and ACE2 as a therapeutic target for the preventive treatment of lung diseases, to reduce the irritability and toxicity of individual components, and to prolong systemic exposure to pentacyclic triterpenoids based on the synergy among its components. Given the background and existing reports on the interaction between glycyrrhizic acid (GA) with the ACE2 and Spike proteins, the inventors decided to test the effects of the combination of GA and its derivative 18β-glycyrrhetinic acid (EN) in the inhibition of this interaction.

The resulting formulations are synergistic compositions whose proportions are designed to reduce toxicological effects, irritability and provide effective pharmacokinetics compared to the application of the same components individually.

The pharmaceutical forms are listed below according to the experimental developments: the preferred forms are solutions, suspensions, and emulsions, as well as the powders and lyophilisates used in their preparation, which are applied through nebulizations, vaporizations and sprays. Although there are several ways to classify the pharmaceutical forms, in this application they are classified considering the route of administration.

Oral administration: Solutions, suspensions, and emulsions for oral administration, as well as solids including tablets, coated tablets, modified release tablets, chewable tablets, capsules, soft capsules, hard capsules.

Cutaneous administration: Solutions, suspensions, foams, pastes, spray powders (powders, solutions and suspensions administered by spray), gels, creams, ointments, patches, and intradermal implants.

Nasal administration: Drops formed by solutions, suspensions, and emulsions. Solution, emulsion, and suspension type spray. Nasal powders, administration gels and nasal ointments.

Injectables: Injectable solutions, suspensions, and emulsions. Powders used to prepare injectable solutions, suspensions, and emulsions. Lyophilizates used to prepare injectable solutions, suspensions, and emulsions.

Respiratory tract: Liquids such as nebulization solutions, suspensions, and emulsions. Liquids such as vaporization solutions, suspensions, and emulsions. Solids such as powders and lyophilizates for administration through oropharyngeal routes.

DETAILED DESCRIPTION OF THE INVENTION

This invention relates to pharmaceutical compositions adapted to be administrable for nasal, cutaneous, oral, injection or inhalation administration to be used in the prevention, treatment, and post-treatment of respiratory tract diseases. These compositions comprise synergistic combinations of pentacyclic triterpenoids together with suitable and pharmaceutically acceptable excipients for the different administration routes. These pharmaceutical compositions are based on the unexpected synergistic effect from some combinations of specific pentacyclic triterpenoids ratios. The compositions described herein are especially effective in the treatment of viral infections, in particular those infections transmitted through interaction between the virus and the angiotensin-converting enzyme 2 (ACE2).

The different compositions of this invention contain at least two pentacyclic triterpenoids. Specifically, glycyrrhizic triterpenoids are referred to as the group of molecules comprising glycyrrhizic acid (also designated as GA), its aglycone, 18β-glycyrrhetinic acid (also designated as EN), and derivatives thereof, in the form of acids, salts, esters, and other derivatives. Regarding the glycyrrhizic triterpenoid group of this formulation, the combination of glycyrrhizic acid (GA) and 18β-glycyrrhetinic acid (EN) is preferably used due to its inhibitory effect on the interaction pathway between the Spike protein (S) of the virus and the angiotensin converting enzyme 2 (ACE2).

The experiments performed consisted on testing the ELISA RayBio COVID-19 Spike-ACE2 binding assay kit (Catalog Number: CoV-SACE2-1), described as an assay for the detection of antibodies and drugs against the COVID-19 disease. This assay seeks to quantify the formation of the ACE2-Spike complex and how it is affected by the presence of a specific drug.

Figure 1:
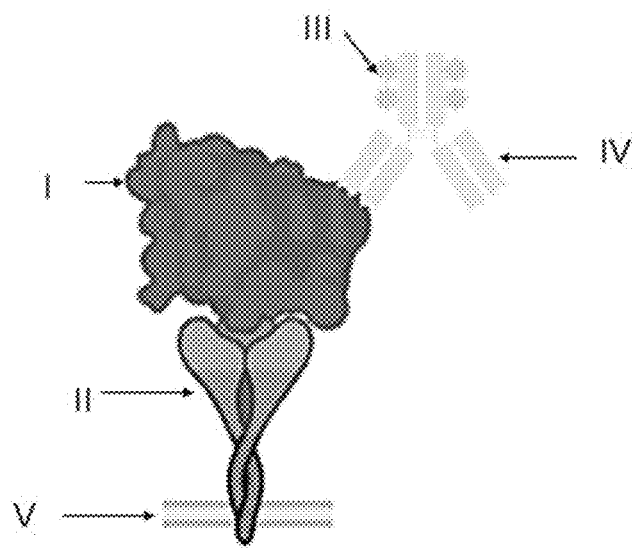
FIG. 1. Spike-ACE2 COVID-19 assay scheme: Spike-ACE2 Complex. If there is interaction between the ACE2 protein (II) and the SPIKE protein (I), the anti-SPIKE antibody (IV) coupled to the HRP enzyme (III) will bind itself to the Spike protein (I). This complex will generate a color change in the ELISA assay (Plate V), which can be quantified.
Figure 2:
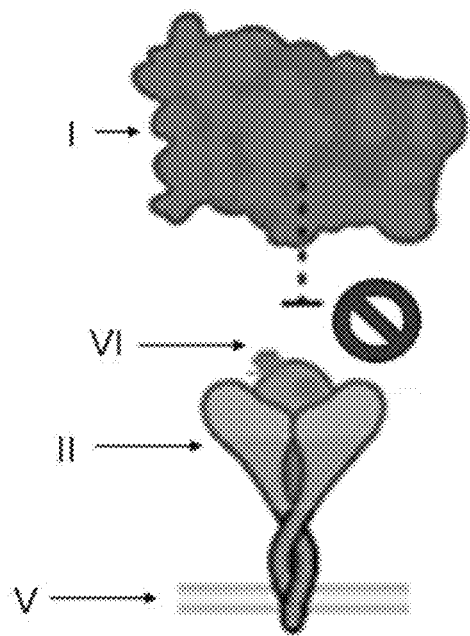
FIG. 2. Spike-ACE2 COVID-19 assay scheme: Inhibition of the SPIKE-ACE2 complex. In the presence of an inhibitory molecule (VI), such as glycyrrhizinic acid or enoxolone, the interaction between the SPIKE protein (I) and the ACE2 protein (II) is interrupted.
Figure 3:
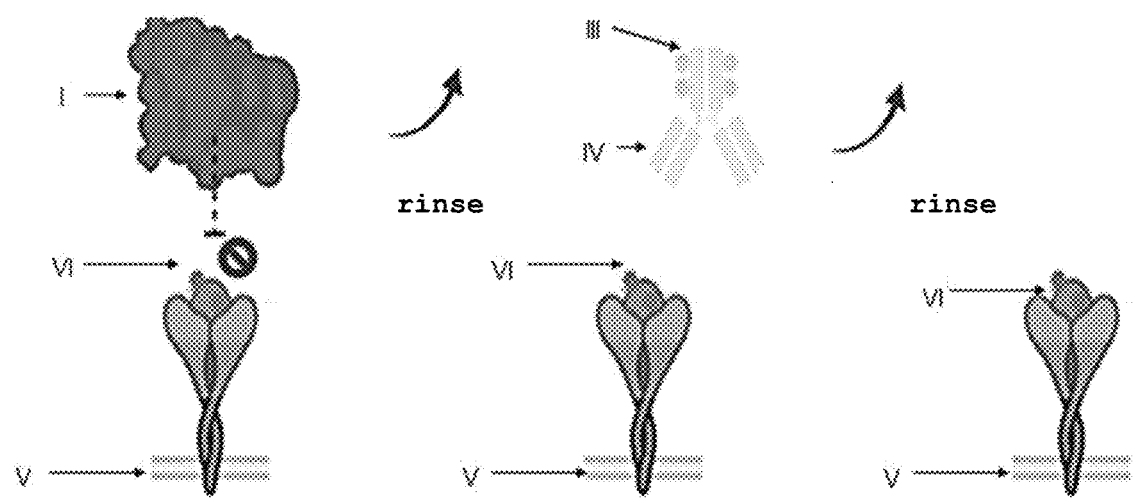
FIG. 3. Spike-ACE2 COVID-19 assay scheme: Upon the presence of an inhibitor (VI), the SPIKE-ACE2 complex is not formed. Hence, the conjugated antibody does not couple with the HRP enzyme (III), and there is no quantifiable color change in the ELISA assay (plate V).

The assay is detailed in FIGS. 1 to 3, which outline the COVID-19 Spike-ACE2 assay. FIG. 1 shows the Spike-ACE2 complex formed in absence of an inhibitor. FIG. 2 shows how the formation of the Spike-ACE2 complex is blocked due to the presence of an inhibitory molecule (VI). Furthermore, FIG. 3 shows that, if the drug of interest affects the formation of the Spike-ACE2 complex, the interaction complex will not be formed, and there will be no quantifiable color change. Conversely, if the drug does not inhibit complex interaction, a strong color signal will be obtained.

Figure 4:
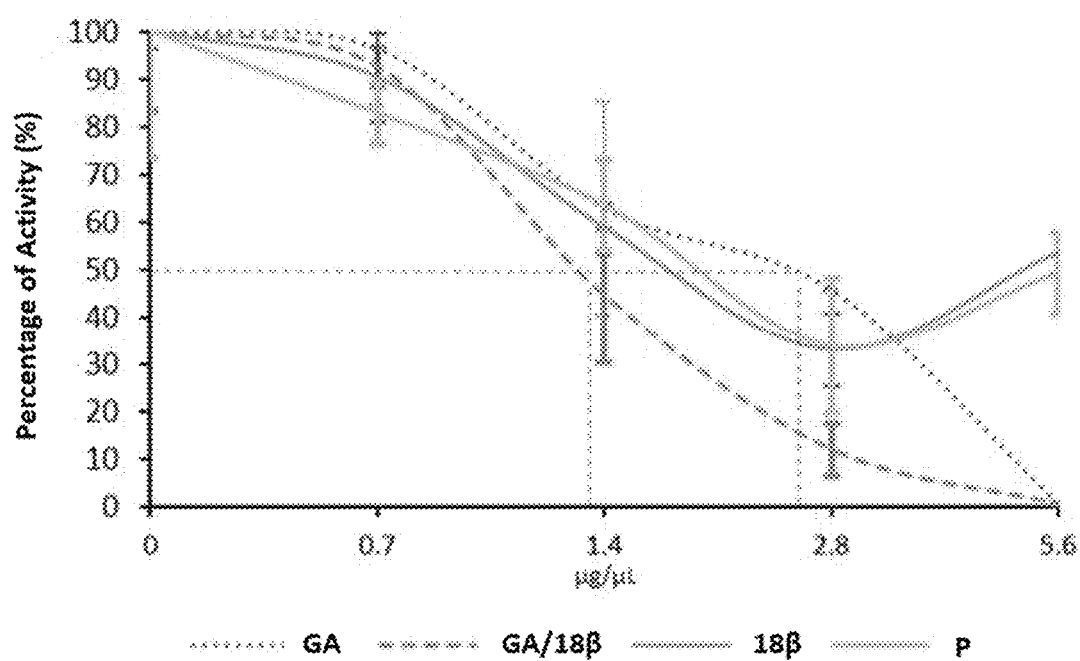
FIG. 4. ELISA assay graph denoting inhibition quantification (or percentage of activity) between the ACE2 protein and the SPIKE protein.

FIG. 4 shows the behavior of the tested composition in ELISA assays for inhibition quantification (percentage of activity) between the ACE2 protein and the SPIKE protein at different concentrations of glycyrrhizic acid (AG) alone, 18β-glycyrrhetinic acid (EN) alone, a blank (P), and the AG-EN combination in proportions within the 1:3 to 1:25 range, and preferably within the 1:5 to 1:20 range. In these assays, the triterpenoid combination proved more effective than the use of the active ingredients separately. This derives in the technical advantage that the use of a lower concentration of both drugs results in obtaining an improvement related to the therapeutic effect.

Figure 5:
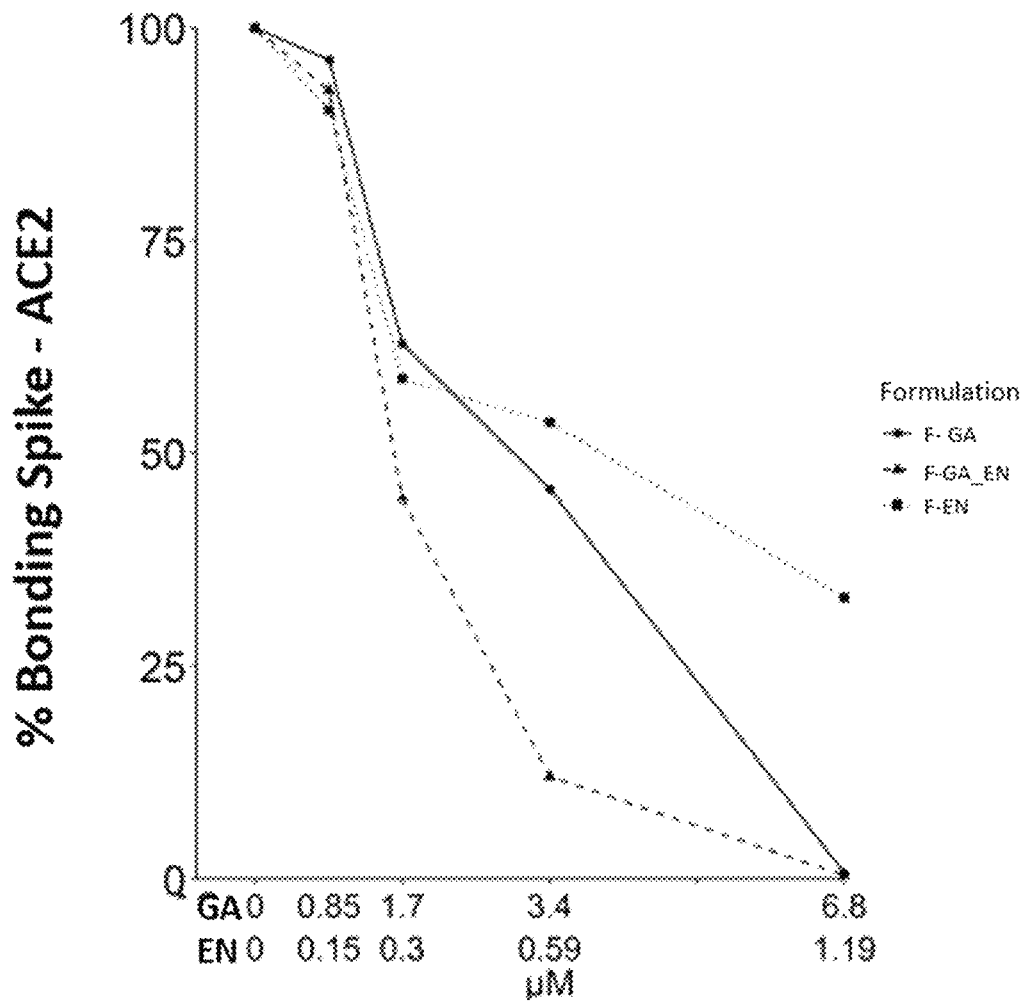
FIG. 5. Results from the inhibition of the ACE2-Spike complex formulation derived from the exposure of the ACE2 protein to GA, EN and their combination.

FIG. 5 shows results of the inhibition of the ACE2-Spike complex formulation derived from the exposure of the ACE2 protein to GA, EN and their combination. Here, the X-axis denotes two different scales, corresponding to the concentration in micromoles (μM) of the GA and EN compounds. It is important to note that the GA-EN combination in proportions within the 1:3 to 1:25 range, and preferably within the 1:5 to 1:20 range, turns out to be clearly more effective than the use of the active principles individually.

FIG. 5 shows different concentrations for both drugs (glycyrrhizic acid (GA) and 18β-glycyrrhetinic acid (EN)) and the binding percentage of the Spike-ACE2 complex detected at each of these concentrations. The graph shows the 3 formulations with the active ingredient. The square dotted line (F-EN) denotes the behavior of the EN formulation; continuous line with circles (F-GA) the GA formulation; and the triangular dashed line denotes the GA-EN formulation. In the lower part, the concentrations in micromoles (μM) of both drugs are shown, these concentrations are valid for the three formulations (GA concentrations are valid for the F-GA and F-EN, and the EN concentrations are valid for F-EN and F-GA-EN). It is important to highlight that the ratio between the GA concentration and the EN concentration is ~5.7:1, (when there is approximately 88% inhibition) in molar terms; while this ratio is 10 to 1 (AG with respect to enoxolone (EN)) in terms of mass, achieving significant inhibition at lower applied doses.

The formulations described herein, in addition to the glycyrrhizic triterpenoids, contain pharmaceutically acceptable excipients that provide the pharmacological properties required to be administrable to humans. Specifically, this invention contains components such as ionic solubilizers, surfactants, non-ionic solubilizers, solvents, pH regulators, osmotic regulators, chelating agents, antioxidants, and preservatives.

In the present invention, ionic solubilizers are defined as the group selected from propylene glycol, glycerin/PEG, poloxamer, polyoxylglyceride derivatives (Labrasol), glyceryl isostearate/glyceryl monostearate, glycerol derivatives, polyethylene glycol 660 12-hydroxystearate, castor oil, and the derivatives thereof. Surfactants are defined by the invention as including, but not strictly limited to, polysorbate, sorbitan monostearate, sorbitol esters, polysorbate 20,60,80 (derivatives of fatty acid esters of sorbitan and polyoxyethylene). The invention also defines nonionic solubilizers as group selected from diethylene glycol monoethyl ether, and the solvents as the group selected from ethanol and water.

Optionally, these formulations can be subjected to pH treatments using HCl, NaOH or any salt and combinations thereof that form an indicated buffer. To adjust the pH level between formulations, an osmolarity adjuster, such as NaCl, dextrose, mannitol, and sorbitol, may be used. The formulations can also contain preservative elements such as benzalkonium chloride, ethanol, propylene glycol, benzyl alcohol, chlorobutanol, paraben derivatives. The compositions may include chelating agents such as EDTA and its derivatives, citric acid and its derivatives, oxalic acid and its derivatives, and ascorbic acid and its derivatives. These compositions may also include viscosity-adjusting components, such as a poloxamer in different degrees of polymerization, microcrystalline cellulose and its derivatives, and antioxidants such as L-cysteine, butylhydroxytoluene, butylhydroxyanisole.

In a preferred embodiment, the formulation uses a combination of GA and EN, with GA concentrations from 0.1% to 20% (m/m), and EN concentration from 0.01% to 4% m/m, and preferably a GA concentration ranging between 0.1% and 10% (m/m) and an EN concentration ranging between 0.01% and 2% m/m. In this embodiment, the formulation uses propylene glycol as an ionic solubilizer in concentrations of 70% to 80% (m/m), polysorbate as a surfactant in concentrations of 0.1 to 7% (m/m), diethylene glycol monoethyl ether as a non-ionic solubilizer in concentrations of 1% to 6% (m/m), and 10% to 20% (m/m) water as a solvent. In this embodiment, the pH level is adjusted to values between 4.0 and 9.0, and preferably between 4.5 and 6.5, using one or more of the aforementioned elements.

As per the foregoing, the disclosed pharmaceutical composition comprises: a synergistic combination of at least two pentacyclic triterpenoids in a 1:3-to-1:25 ratio for the treatment of viral infections.

In other embodiments, viral infections are viral respiratory infections.

In other embodiments, the composition comprises at least one pharmaceutically acceptable additive, wherein the pentacyclic triterpenoids are glycyrrhizinic acid and 18β-glycyrrhetinic acid and are found in a ratio preferably with the 1:5-to-1:20 range.

In other embodiments, the pharmaceutical composition exhibits a glycyrrhizinic acid content of 0.1% to 20% and a 18β-glycyrrhetinic acid content of 0.01% to 4%, and preferably a GA concentration of 0.1% to 10% m/m and an EN concentration of 0.01% to 2% m/m.

In other embodiments, the pharmaceutical composition contains a synergistic combination within the composition, which is in the range exceeding 0.0% to 30%, preferably in the 0.01%-to-10% range.

In other embodiments, pharmaceutically acceptable additives comprise ionic and nonionic solubilizers, surfactants, and solvents; wherein ionic solubilizers are selected from the group comprising: propylene glycol, glycerin/PEG, poloxamer, polyoxylglyceride derivatives (Labrasol), glyceryl isostearate/glyceryl monostearate, glycerol derivatives, polyethylene glycol 660 12-hydroxystearate, castor oil and its derivatives, and are found in a concentration of 70% to 80% m/m.

In other embodiments, the pharmaceutical composition comprises surfactants selected from the group comprising: polysorbate, sorbitan monostearate, sorbitol esters, polysorbate 20,60,80, and are found in concentrations of 0.1% to 7%.

In other embodiments, the pharmaceutical composition comprises diethylene glycol monoethyl ether as a non-ionic solubilizer in a concentration of 1% to 6%, and 10% to 20% water as a solvent.

EXAMPLES

In the different assays performed, the following formulations were tested:

Formulation 1: Nebulizable 2.8% AG solution
Formulation 2: Nebulizable 0.28% EN solution
Formulation 3: Nebulizable 2.8% AG-0.28% EN solution.
Formulation 4: Excipients or blank nebulizable solution.

In addition to containing the active ingredients (GA, EN), the respective formulations contain:

70 to 80% propylene glycol; preferably 73 to 77% m/m.
0.1 to 7% polysorbate; preferably 4 to 6% m/m.
1 to 6% diethylene glycol monoethyl ether; preferably 3 to 5% m/m.
Water, balance at 100% m/m.

The different formulations were tested in 4 different dilutions, starting from the original concentrations, and preparing 3 additional 1:1 dilutions. The concentrations used in the study are shown in the following table:

TABLE 1

| Dilution | Formulation 1 (AG μg) | Formulation 2 (EN μg) | Formulation 3 (AG-EN μg) | Formulation 4 (Excipients) |
|---|---|---|---|---|
| 1 | 5.6 | 0.56 | 5.6-0.56 | 1 (UR) |
| 2 | 2.8 | 0.28 | 2.8-0.28 | 0.5 |
| 3 | 1.4 | 0.14 | 1.4-0.14 | 0.25 |
| 4 | 0.7 | 0.07 | 0.7-0.07 | 0.125 |

TABLE 2

| Formulation | Component | Composition (%) m/m | GA:EN Ratio |
|---|---|---|---|
| Formulation 1 | GA | 2.8% | 1:0 |
| | EN | 0% | |
| | Polyethylene glycol | 73-77% | |
| | Polysorbate | 4-6% | |
| | Diethylene glycol | 3-5% | |
| | Water | Balance | |
| Formulation 2 | GA | 0% | 0:1 |
| | EN | 0.28% | |
| | Polyethylene glycol | 73-77% | |
| | Polysorbate | 4-6% | |
| | Diethylene glycol | 3-5% | |
| | Water | Balance | |
| Formulation 3 | GA | 2.8% | 10:1 |
| | EN | 0.28% | |
| | Polyethylene glycol | 73.62% | |
| | Polysorbate | 5% | |
| | Diethylene glycol | 4.3% | |
| | Water | 14% | |
| Formulation 4 | GA | 0% | 0:0 |
| | EN | 0% | |
| | Polyethylene glycol | 73-77% | |
| | Polysorbate | 4-6% | |
| | Diethylene glycol | 3-5% | |
| | Water | Balance | |

Tables 1 and 2 show comparative formulations containing GA and EN individually, and specifically in formulation 3 a 1:10 ratio between EN-GA is indicated for the SPIKE-ACE2 protein inhibition assay.

Results

As a result from the experiment, the following values were obtained in terms of the inhibition percentage for the Spike-ACE2 complex.

TABLE 3

| Formulation | EN μg | EN μM | AG μg | AG μM | Dilution | Binding % | Inhibition % |
|---|---|---|---|---|---|---|---|
| F-AG | 0 | 0.00 | 5.6 | 6.80 | 1 | 0.69 | 99.31 |
| F-AG | 0 | 0.00 | 2.8 | 3.40 | 0.5 | 45.77 | 54.23 |
| F-AG | 0 | 0.00 | 1.4 | 1.70 | 0.25 | 62.81 | 37.19 |
| F-AG | 0 | 0.00 | 0.7 | 0.85 | 0.125 | 96.28 | 3.72 |
| F-AG | 0 | 0.00 | 0 | 0.00 | 0 | 100 | 0 |
| F-EN | 0.56 | 1.19 | 0 | 0.00 | 1 | 33.02 | 66.98 |
| F-EN | 0.28 | 0.59 | 0 | 0.00 | 0.5 | 53.63 | 46.37 |
| F-EN | 0.14 | 0.30 | 0 | 0.00 | 0.25 | 58.73 | 41.27 |
| F-EN | 0.07 | 0.15 | 0 | 0.00 | 0.125 | 90.37 | 9.63 |
| F-EN | 0 | 0.00 | 0 | 0.00 | 0 | 100 | 0 |
| F-AG-EN | 0.56 | 1.19 | 5.6 | 6.80 | 1 | 0.49 | 99.51 |
| F-AG-EN | 0.28 | 0.59 | 2.8 | 3.40 | 0.5 | 12.01 | 87.99 |
| F-AG-EN | 0.14 | 0.30 | 1.4 | 1.70 | 0.25 | 44.56 | 55.44 |
| F-AG-EN | 0.07 | 0.15 | 0.7 | 0.85 | 0.125 | 92.69 | 7.31 |
| F-AG-EN | 0 | 0.00 | 0 | 0.00 | 0 | 100 | 0 |
| EX | 0 | 0.00 | 0 | 0.00 | 1 | 49.24 | 50.76 |
| EX | 0 | 0.00 | 0 | 0.00 | 0.5 | 33.85 | 66.15 |
| EX | 0 | 0.00 | 0 | 0.00 | 0.25 | 63.5 | 36.5 |

TABLE 3-continued

| Formulation | EN μg | EN μM | AG μg | AG μM | Dilution | Binding % | Inhibition % |
|---|---|---|---|---|---|---|---|
| EX | 0 | 0.00 | 0 | 0.00 | 0.125 | 82.84 | 17.16 |
| EX | 0 | 0.00 | 0 | 0.00 | 0 | 100 | 0 |

One of the problems with GA is the rapid metabolism it undergoes when administered orally or though injection to humans. For this reason, it has been suggested that oral or injected GA administration may not achieve the local concentrations required for a therapeutic effect. Likewise, the concentrations necessary to generate therapeutic antiviral effects are extremely high to be considered as a drug. Hence, this application describes the characteristics of the invention, assessing the toxicological effects and local irritability in the use of the synergistic composition by the inhaled route in murine.

Tables 4 and 5 evidence comparative formulations containing GA and EN individually and the AG-EN combination in a toxicity and irritability assay in murine rodents.

TABLE 4

| | Control Not applicable | GA | | AG-EN | | EN | |
|---|---|---|---|---|---|---|---|
| Dosage | | Low | High | Low | High | Low | High |
| Drug concentration | Not administered | 4 mg/mL | 10 mg/mL | 4 mg/mL AG + 0.4 mg/mL EN | 10 mg/mL AG + 1 g/mL EN | 0.4 mg/mL | 1 mg/mL |

TABLE 5

| Formulation | Component | Composition (%) m/m | GA:EN Ratio |
|---|---|---|---|
| AG Low | GA | 0.4% | 1:0 |
| | EN | 0% | |
| | Polyethylene glycol | 73-77% | |
| | Polysorbate | 4-6% | |
| | Diethylene glycol | 3-5% | |
| | Water | Balance | |
| AG High | GA | 1% | 1:0 |
| | EN | 0.0% | |
| | Polyethylene glycol | 73-77% | |
| | Polysorbate | 4-6% | |
| | Diethylene glycol | 3-5% | |
| | Water | Balance | |
| EN Low | GA | 0% | 0:1 |
| | EN | 0.04% | |
| | Polyethylene glycol | 73-77% | |
| | Polysorbate | 4-6% | |
| | Diethylene glycol | 3-5% | |
| | Water | Balance | |
| EN High | GA | 0% | 0:1 |
| | EN | 0.1% | |
| | Polyethylene glycol | 73-77% | |
| | Polysorbate | 4-6% | |
| | Diethylene glycol | 3-5% | |
| | Water | Balance | |
| AG-EN Low | GA | 0.4% | 10:1 |
| | EN | 0.04% | |
| | Polyethylene glycol | 76.26% | |
| | Polysorbate | 5% | |
| | Diethylene glycol | 4.3% | |
| | Water | 14% | |
| AG-EN High | GA | 1% | 10:1 |
| | EN | 0.1% | |
| | Polyethylene glycol | 75.6% | |

TABLE 5-continued

| Formulation | Component | Composition (%) m/m | GA:EN Ratio |
|---|---|---|---|
| | Polysorbate | 5% | |
| | Diethylene glycol | 4.3% | |
| | Water | 14% | |

Figure 6:
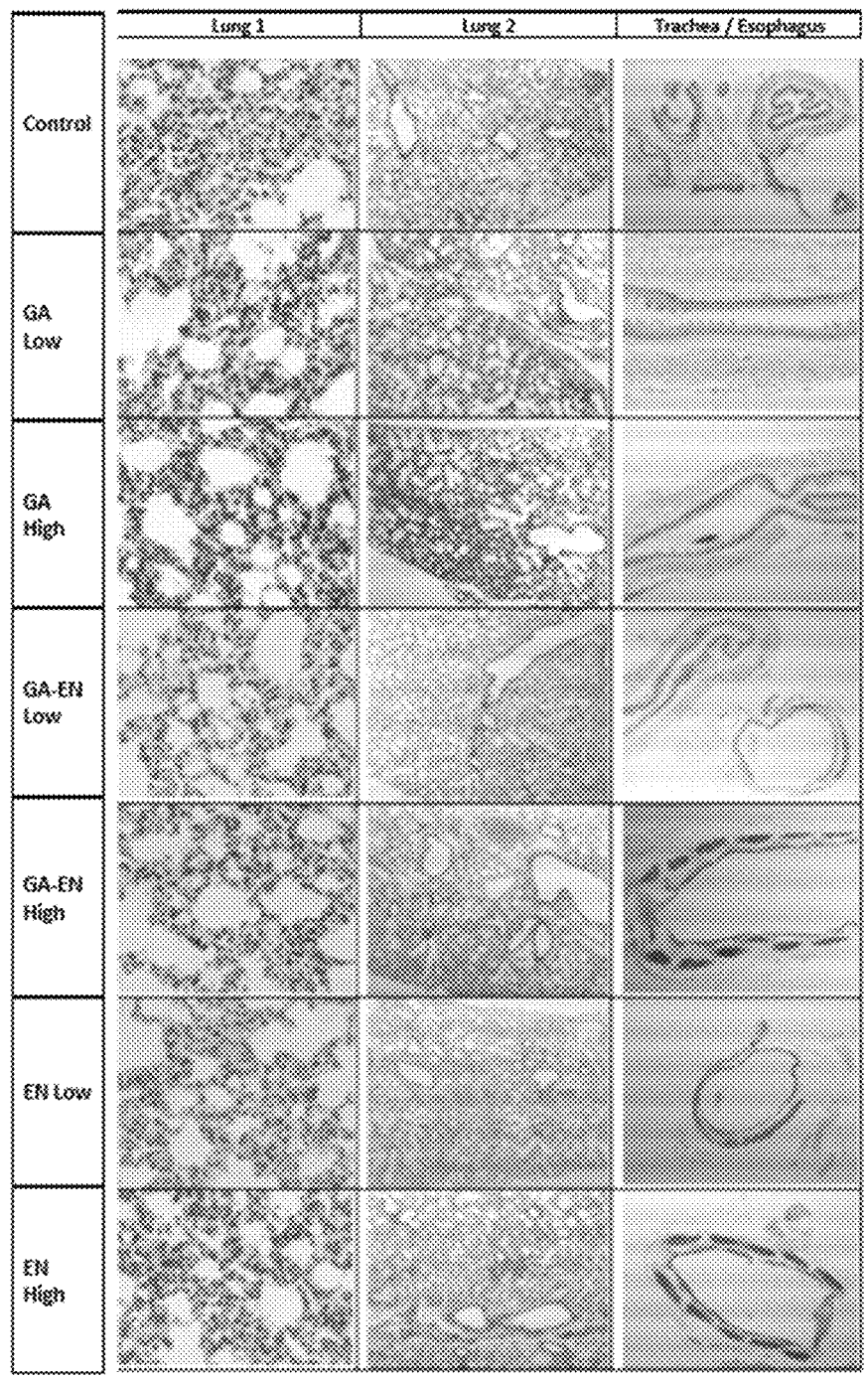
FIG. 6. Images of histopathological sections of murine respiratory tract tissue with application of compositions with AG, EN and a combination of AG-EN.
Figure 7:
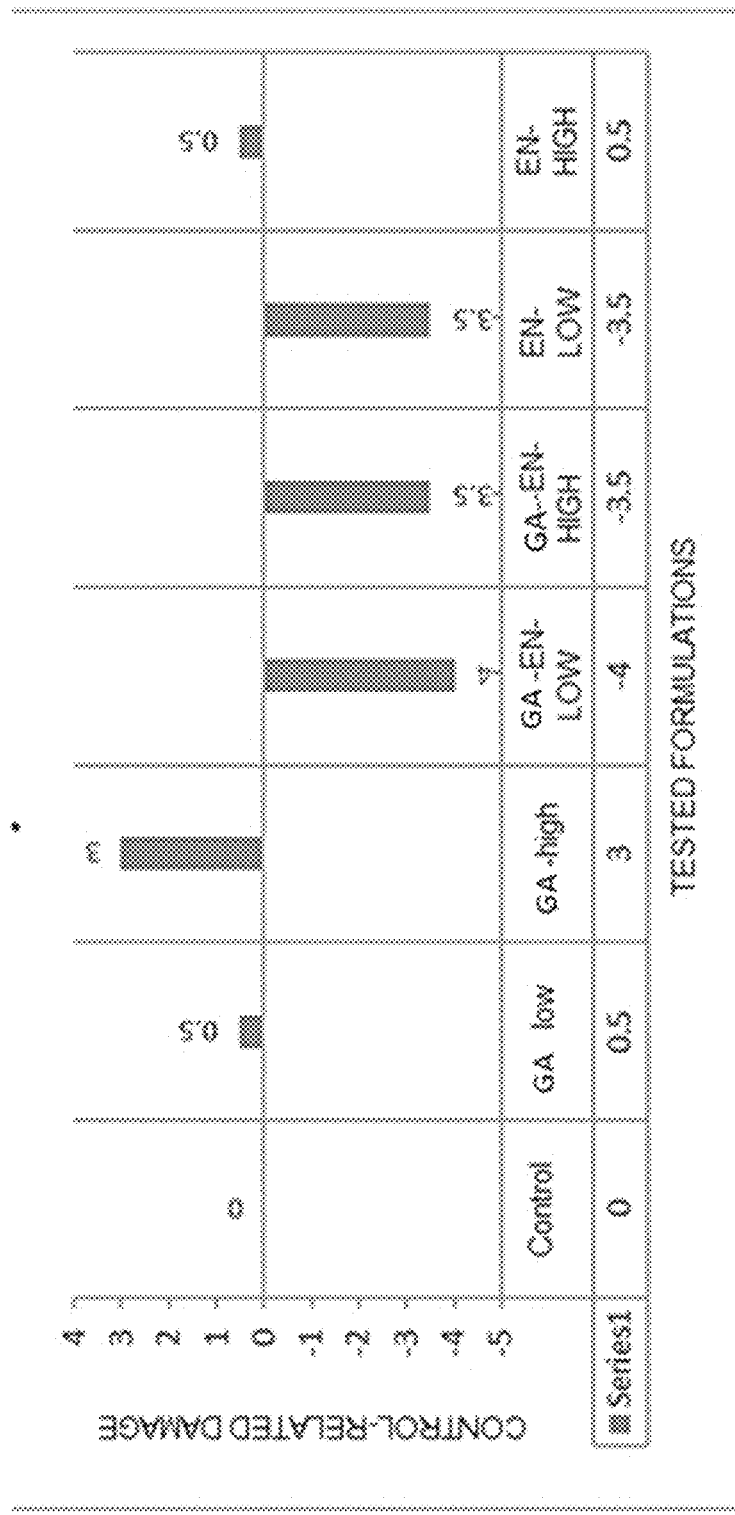
FIG. 7. Standardized table for assessing toxicity and irritability of murine respiratory tract tissue with the application of compositions with AG, EN and a combination of AG-EN.
Figure 8:
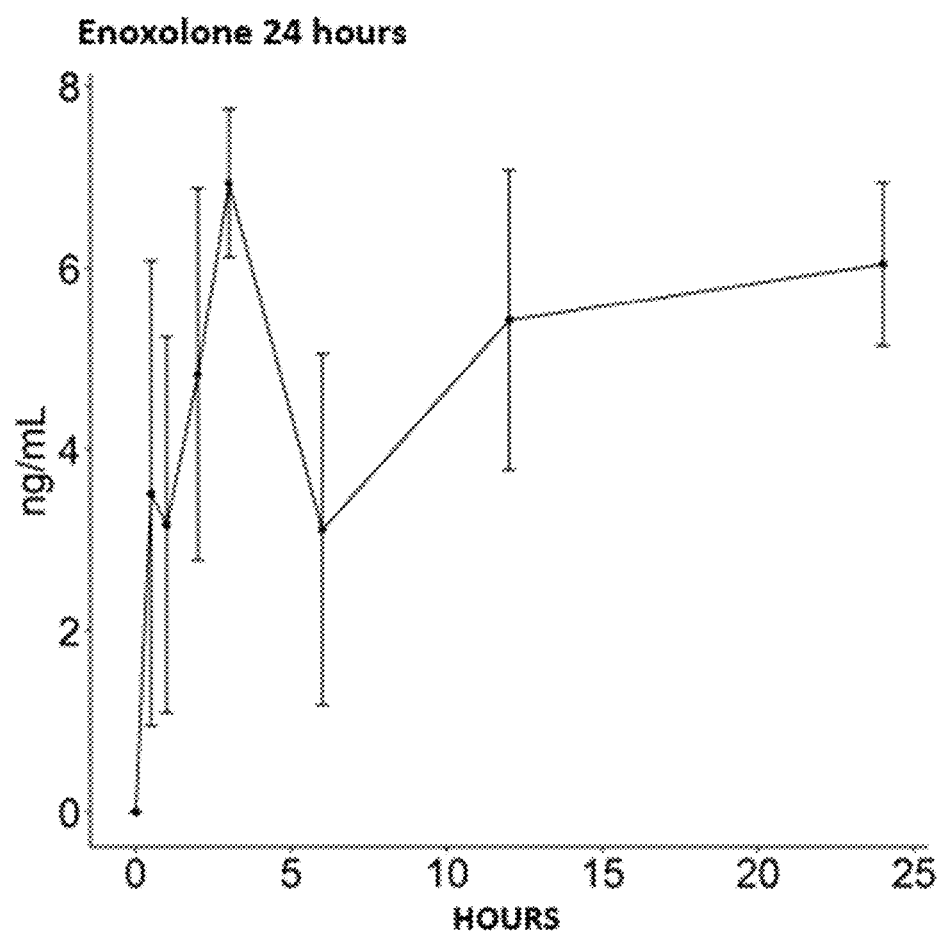
FIGS. 8 and 9. Pharmacokinetic graphs of EN suspensions, corresponding to 24 and 96 hours.
Figure 9:
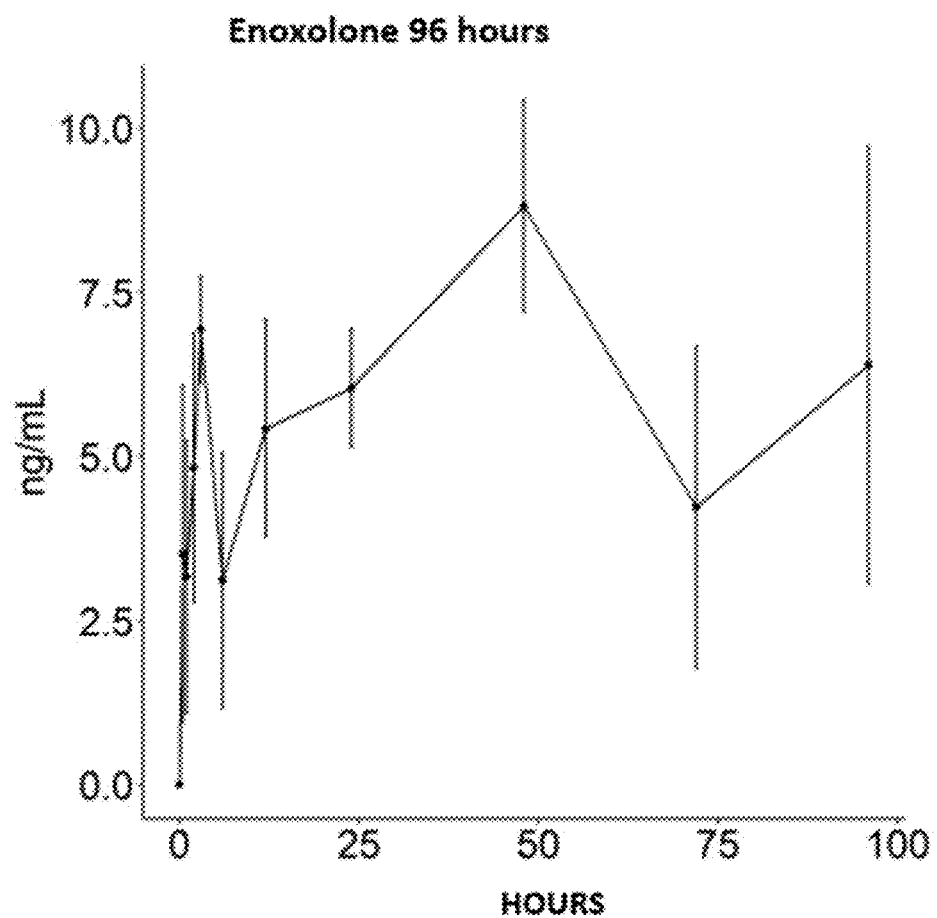
Figure 10:
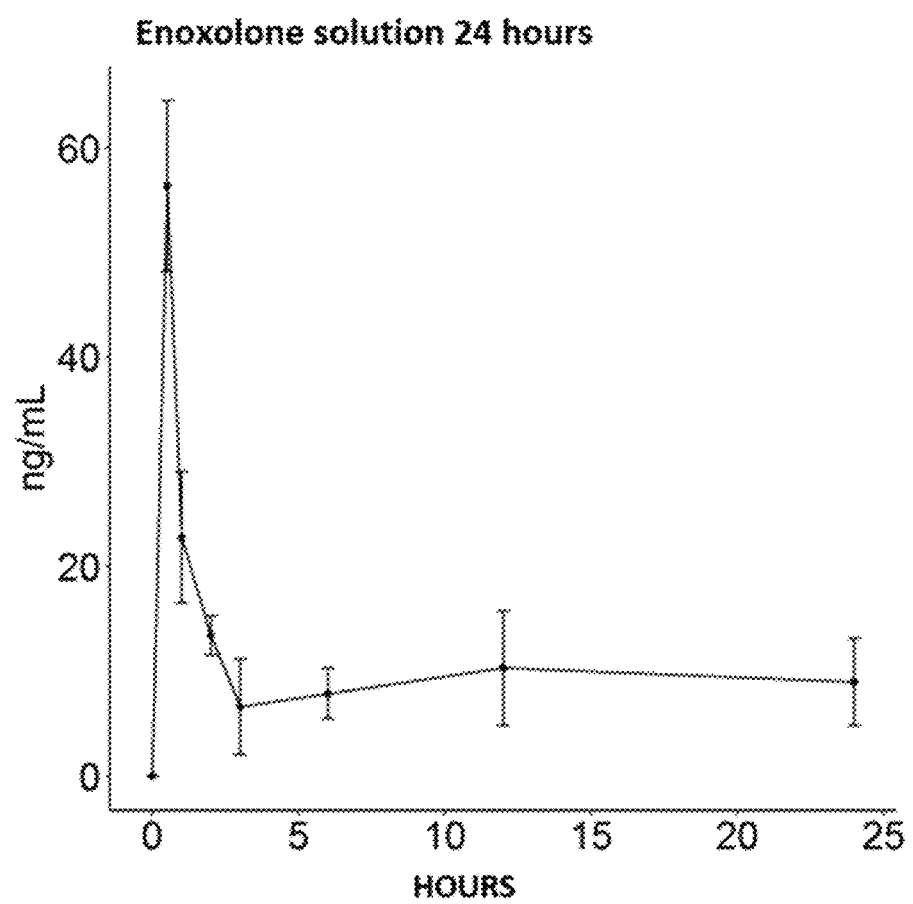
FIGS. 10 and 11. Pharmacokinetic graphs of EN solutions, corresponding to 24 and 96 hours.
Figure 11:
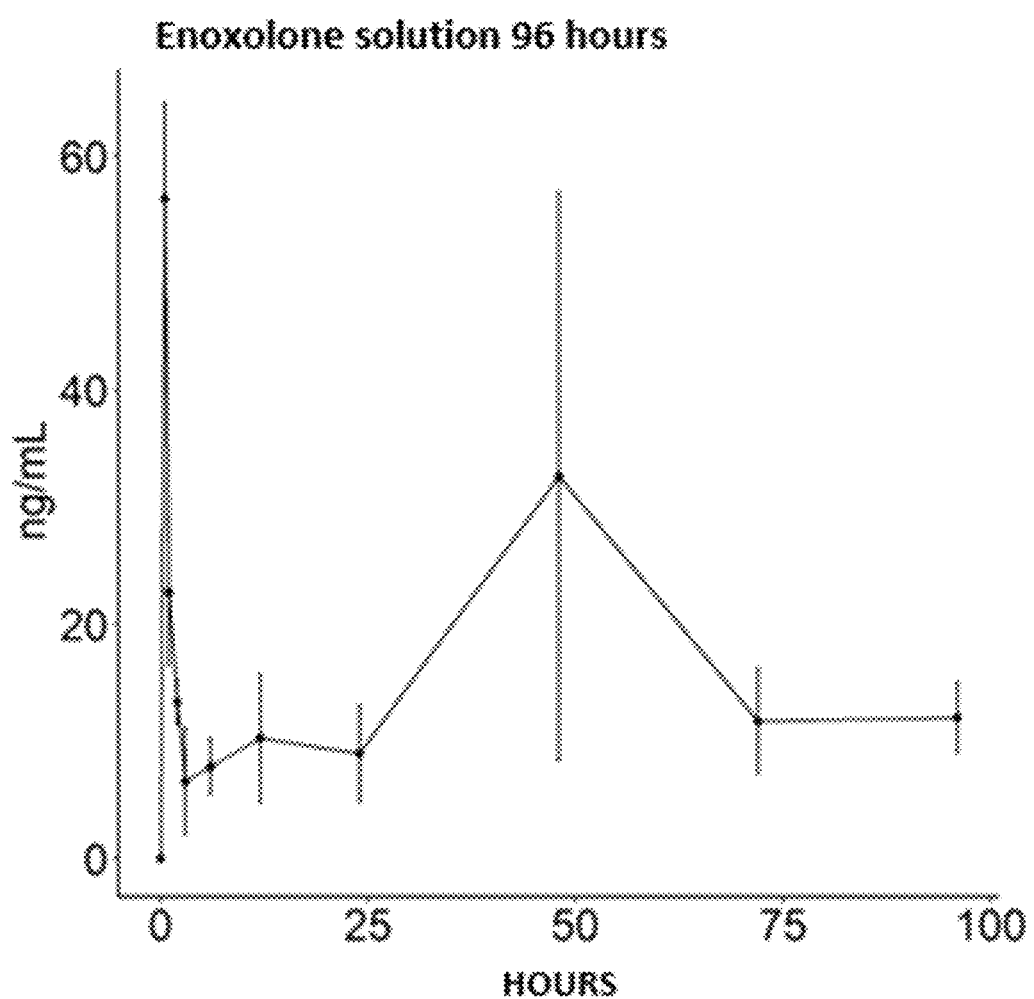

These formulations were administered to groups of murine rodents for 10 minutes a day during 14 consecutive days. Each group was given only one dose type for the entire duration of treatment. At the end of the treatment, the animals were sacrificed, and their respiratory tract tissue was recovered. Lung tissue and the trachea were recovered from one murine rodent from each group. Said tissue was subjected to a histopathological analysis, thereby assessing tissue damage from these samples as follows:

"The alterations observed between the different groups are classified in Table 4 with a subjective score of 0 to 5, wherein 0 means no lesions and 5 corresponds to severe lesions." See FIGS. 6 and 7.

The cuts shown in FIG. 6 were examined and assigned a damage rating based on these criteria. This evaluation is detailed in Table 6:

TABLE 6

| | | GA | | GA-EN | | EN | |
|---|---|---|---|---|---|---|---|
| Lesion | Control | Low | High | Low | High | Low | High |
| Vascular | | | | | | | |
| Congestion | 2 | 2 | 2 | 2 | 2 | 2 | 2 |
| Hemorrhage | 3 | 3 | 2 | 1 | 2 | 1 | 1 |
| Alveolar edema | 0 | 0 | 0 | 0 | 0 | 0 | 0 |
| Interstitial edema | 1 | 1 | 2 | 0.5 | 0.5 | 1 | 2 |
| Thrombosis | 0 | 0 | 0 | 0 | 0 | 0 | 0 |
| Inflammatory | | | | | | | |
| Interstitial Pneumonia | 2.5 | 3 | 3.5 | 2 | 1.5 | 2 | 3 |
| Hyaline Membrane | 0 | 0 | 0 | 0 | 0 | 0 | 0 |
| Bronchiolitis | 0 | 0 | 0 | 0 | 0 | 0 | 0 |
| Bronchitis | 0 | 0 | 0 | 0 | 0 | 0 | 0 |
| Vasculitis | 0 | 0 | 0 | 0 | 0 | 0 | 0 |
| Degenerative | | | | | | | |
| Alveolar | 0 | 0 | 0 | 0 | 0 | 0 | 0 |
| Bronchiolar | 0.5 | 0.5 | 1 | 0 | 0 | 0 | 1 |
| Bronchial | 0.5 | 0.5 | 1 | 0 | 0 | 0 | 1 |
| Necrosis | | | | | | | |
| Alveolar | 0 | 0 | 0 | 0 | 0 | 0 | 0 |
| Bronchiolar | 0 | 0 | 0 | 0 | 0 | 0 | 0 |
| Bronchial | 0 | 0 | 1 | 0 | 0 | 0 | 0 |

TABLE 6-continued

| Lesion | Control | GA Low | GA High | GA-EN Low | GA-EN High | EN Low | EN High |
|---|---|---|---|---|---|---|---|
| Fibrosis | | | | | | | |
| Alveolar Septa | 0 | 0 | 0 | 0 | 0 | 0 | 0 |
| Peribronchiolar | 0 | 0 | 0 | 0 | 0 | 0 | 0 |
| Peribronchial | 0 | 0 | 0 | 0 | 0 | 0 | 0 |
| TOTAL | 9.5 | 10 | 12.5 | 5.5 | 6 | 6 | 10 |

In Table 6, the last row indicates the total damage and lesion rating for each group. These results were standardized by subtracting the control rating (control=9.5). The standardized data are presented in FIG. 7.

The results from FIG. 6 show a series of patterns regarding the different compositions:

The GA composition indicates the generation of additional lesions to the basal lesions, which increases according to the amount of administered drug.

The EN composition indicates a decrease in basal lesions when used at low concentrations. At higher concentrations of this compound, this effect is lost, and it starts to cause additional lesions.

The combination of both drugs indicates a joint beneficial effect greater than what would be expected from their individual effects.

For the low-concentration GA-EN composition (4 mg/mL GA+0.4 mg/mL EN), the expected sum of the individual effects is −3 (−3.5+0.5), and the observed effect is −4.

For the high-concentration GA-EN composition (10 mg/mL GA+1 mg/mL EN), the expected sum of the individual effects is 3.5 (3+0.5), and the observed effect is −3.

The results suggest that there is an unexpected advantage when using a high GA-EN composition (10 mg/mL GA+1 mg/mL EN). On the one hand, it is suggested that the lesions expected from the individual use of its components (value of 3.5) are counteracted by the combination of these, and it is even observed that this combination synergistically reduces pre-existing lesions given the value observed (value of −3.5). In addition, these results also imply that a higher dose would generate a more powerful therapeutic effect.

Alternative tests were conducted to verify the synergistic behavior of the compositions of interest. For this reason, the results of pharmacokinetic studies are described and disclosed herein below. The study was based on the application of different versions of the herein claimed pharmaceutical composition to healthy volunteers by the inhaled route of administration, by means of a nebulizer device. The volunteers were given the drug once every 24 hours for three days. In addition, blood samples were taken from them at different time points. These samples were analyzed to quantify glycyrrhizinic acid (GA) and Enoxolone (EN) contents through the mass coupled HPLC methodology. The study consisted of the application of the following formulations to healthy volunteer subjects:

TABLE 7

| Formulation | Composition (active components) mg/mL | Number of Subjects |
|---|---|---|
| 036COV21 | 3 mg EN, 60 mg AG | 3 |
| 037COV21 | 2 mg EN, 30 mg AG | 2 |
| 038COV21 | 60 mg AG | 3 |
| 039COV21 | 3 mg EN (solution) | 3 |
| 040COV21 | 3 mg EN (suspension) | 3 |

TABLE 8

| Formulation | Component | Composition (%) m/m | GA:EN Ratio |
|---|---|---|---|
| 036COV21 | GA | 6% | 20:1 |
| | EN | 0.3% | |
| | Polyethylene glycol | 70.4% | |
| | Polysorbate | 5% | |
| | Diethylene glycol | 4.3% | |
| | Water | 14% | |
| 037COV21 | GA | 3% | 15:1 |
| | EN | 0.2% | |
| | Polyethylene glycol | 73.5% | |
| | Polysorbate | 5% | |
| | Diethylene glycol | 4.3% | |
| | Water | 14% | |

Tables 7 and 11 evidence comparative formulations containing GA and EN individually and the AG-EN combination in a pharmacokinetic assay.

For the pharmacokinetic study, each subject was administered 1 mL from one of the compositions diluted with 4 mL of saline solution. The resulting mixture was supplied through a Nebucore P-103 nebulizer for approximately 20 minutes or until the solution was completely nebulized (whichever came first). Subjects were given a second and third dose at 24 and 48 hours, respectively.

Blood samples of 5 mL were taken from each of the individuals at 30 minutes and at 1, 2, 3, 6, 12, 24, 48, 72 and 96 hours after drug administration. Then, the AG and EN concentrations in these blood samples were determined using the mass coupled HPLC methodology. In all cases, both components were quantified. The corresponding results are listed below.

The following tables denote pharmacokinetic results (Area Under the Curve (AUC)) of the two drugs assessed (GA and EN). The Area Under the Curve (AUC) is a parameter related to the drug quantity to which the body has been exposed. Results were obtained by analyzing plasma concentrations after 24 hours. The AUC was calculated using the R programming language within the "PK" software bundle. For these calculations, a single-compartment model was assumed.

AUC Enoxolone 24 Hours

TABLE 9

| Formula | AUC (0 ≥ t) |
|---|---|
| 036COV21 | 3594.573387 |
| 037COV21 | 1258.471472 |
| 038COV21 | 664.5081426 |
| 039COV21 | 253.4182813 |
| 040COV21 | 121.8772356 |

AUC AG 24 Hours

TABLE 10

| Formula | AUC (0 ≥ t) |
|---|---|
| 036COV21 | 6510.27298 |
| 037COV21 | 9372.097 |
| 038COV2 | 2297.631 |
| 039COV21 | NA |
| 040COV21 | NA |

FIGS. 8 to 21 denote graphs corresponding to concentration changes in the blood samples over time. The respective formulations are applied at two different time periods: 24 and 96 hours. The assessments and conclusions mentioned correspond to the 24-hour graphs. We used 24 hours, because most samples collected (30 minutes, 1, 2, 3, 6, 12 and 24 hours) characterize the pharmacokinetic behavior of the formulations from the first intake (0 hours) until before the second administration (24 hours).

FIGS. 8, 9, 10 and 11 show, respectively, the pharmacokinetic graphs of EN in suspension 040COV21 (FIGS. 8 and 9) and EN in solution 039COV21 (FIGS. 10 and 11) corresponding to 24 and 96 hours.

Figure 12:
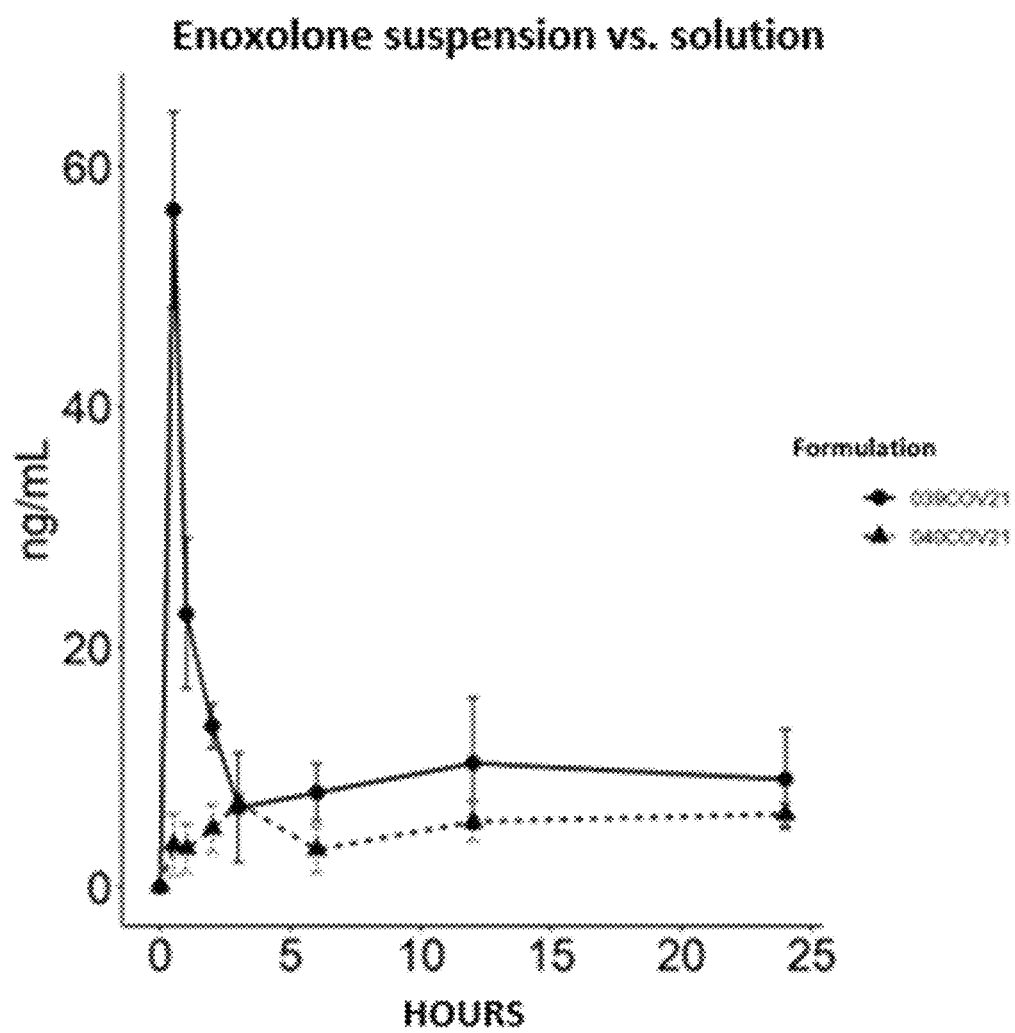
FIG. 12. Pharmacokinetic graphs of EN suspensions vs solutions, corresponding to 24 hours.

FIG. 12 shows a comparative graph of the pharmacokinetics of EN in suspension vs. EN in solution corresponding to 24 hours. In this FIG. 12, the nebulization Enoxolone suspension (including undissolved particles) denotes smaller areas under the curve than the nebulization Enoxolone solution (completely dissolved particles). These results delimit and confirm the virtues between the selection of a pharmaceutical form in terms of drug absorption), and the effect produced by the reduction of the particle size of the drugs that potentiates the permeation either by diffusion, transport, or ion exchange; additionally, it is indicated that the smaller the particle size and a moderate permeability, the greater the absorption. Another point to consider in the selection of the Pharmaceutical Form (PF) and the administration route, wherein not only the biopharmaceutical and physicochemical properties influence in the product administration, but also the selection of the supplies or excipients will modulate the delivery, stability, reproducibility, and administration of the drug.

Figure 13:
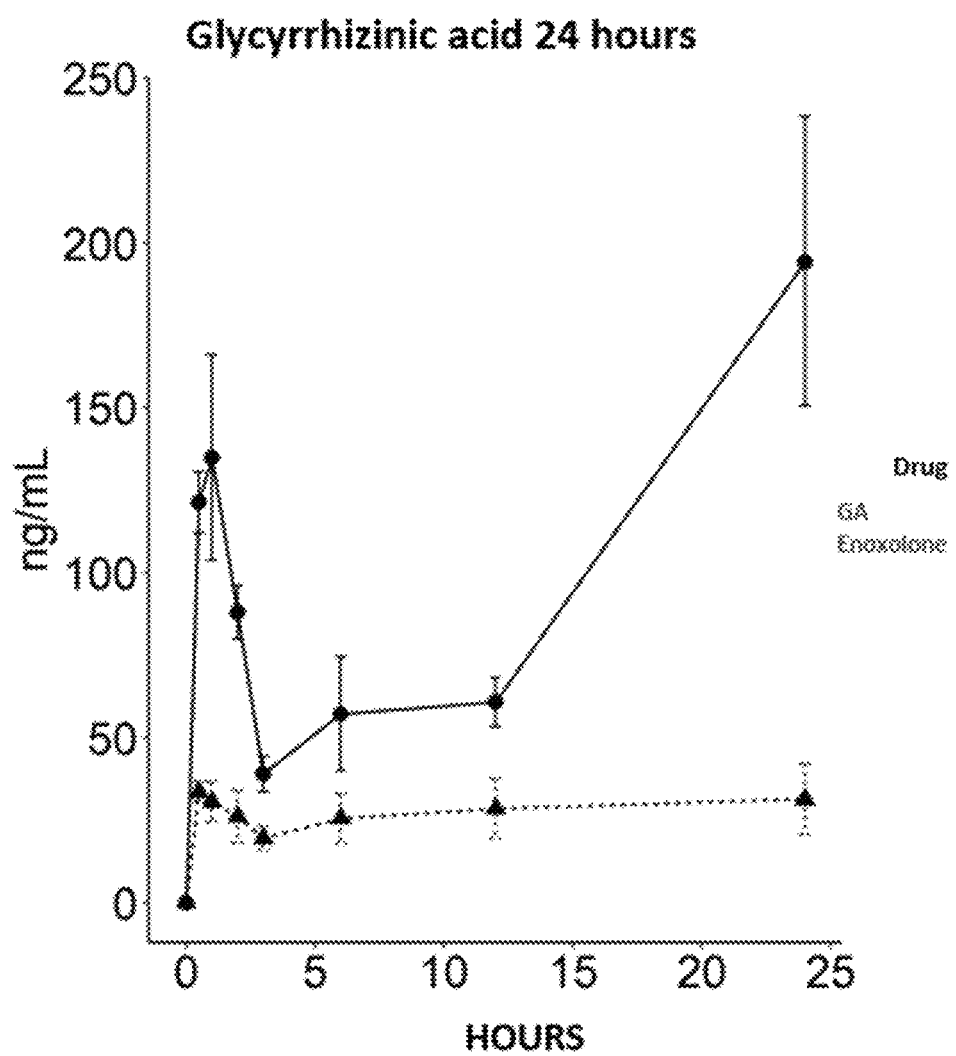
FIGS. 13 and 14. Pharmacokinetic graphs of AG solutions, corresponding to 24 and 96 hours FIGS. 15 and 16. Pharmacokinetic graphs for combination of 30 mg GA and 2 mg EN (ratio 15:1) (037COV21), corresponding to 24 and 96 hours.
Figure 14:
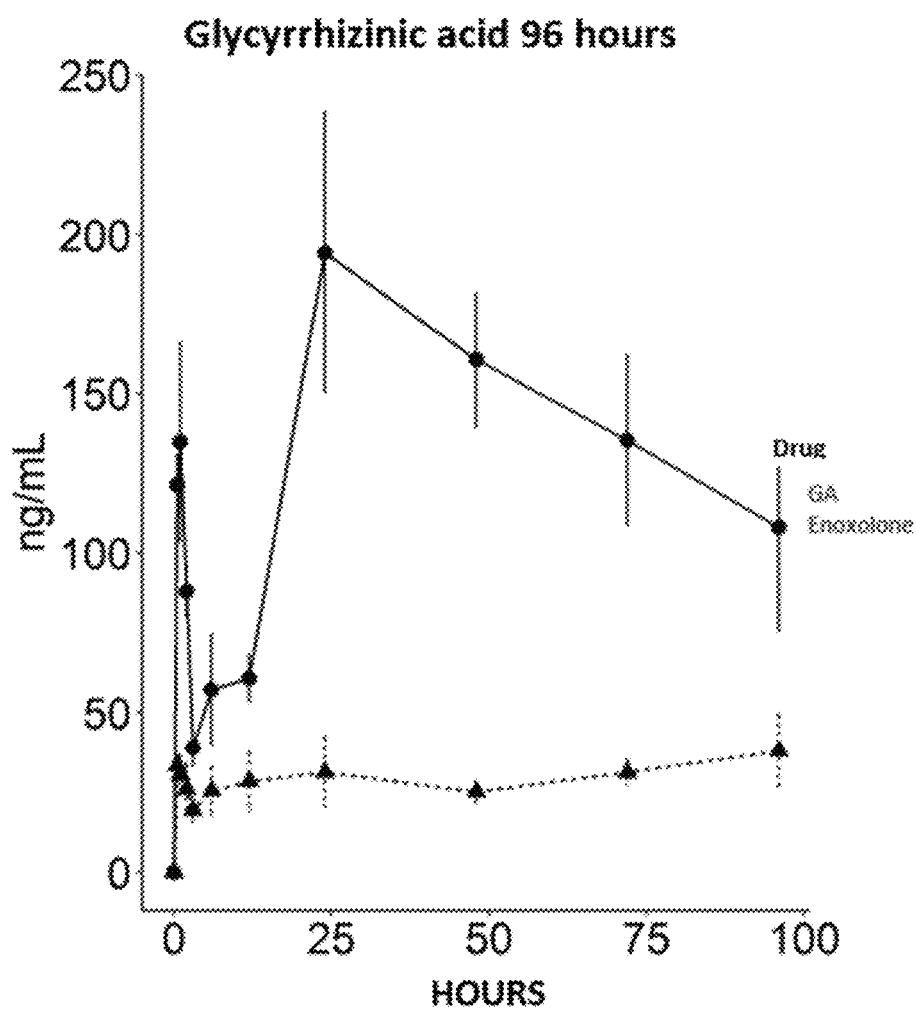

For the specific case of glycyrrhizic acid (GA), its absorption by inhalation route depends on the pharmaceutical form used since, although GA is soluble in water, it exhibits reduced permeability. Hence, both the excipients and its manufacturing process will limit its absorption capabilities. Regarding the results obtained, FIGS. 13 and 14 show two absorption curves: one close to 24 hours after the application of the product and the second at 96 hours, thus observing a representative effect from the modified release pharmaceutical form. This effect can be correlated to said pharmaceutical form and to the administration route, wherein it is estimated that the airways remain impregnated with GA for more than 24 hours; additionally an initial peak value is observed at 60 min, characteristic for an oral administration (gastrointestinal absorption) and in which GA is bio transformed into EN, a metabolite that will undergo a second metabolism in the liver to be subsequently removed from the organism. On the other hand, the data obtained reveal that GA elimination is delayed for a longer time when administered by inhalation, thus denoting a bicompartmental behavior also observed when the drug is administered by injection and being very different from oral administration (two ascending plateaus), which starts elimination after 6 hours. On the other hand, regarding the advantages of the formulation developed, a low-viscosity solution was obtained, which provides an advantage over other pharmaceutical forms with similar concentrations since products with high concentrations tend to form gels due to the effect of the glycyrrhizinic acid (GA).

In FIGS. 13 and 14, there is a presence of EN. This is because, as mentioned above, GA is bio transformed (hydrolyzed) into EN to be first metabolized in the liver and subsequently eliminated from the body. Moreover, the concentration obtained by inhalation is much lower than the concentration obtained by oral administration (200.3 ng/mL when 75 mg of GA is administered), which is an indicator of the biotransformation that occurs in the gastrointestinal tract. Hence, when GA is absorbed without passing through the gastrointestinal tract, its metabolism into EN is reduced, and only the fraction that passes through this tract is then metabolized.

Due to the above, it can be pointed out that the administration of GA by air route (in a nebulized solution) provides an initial surface effect in the upper airways, exerting its antimicrobial and antiviral effect to subsequently produce a lengthened systemic effect (greater than 24 hours) with reduced biotransformation into EN.

Figure 15:
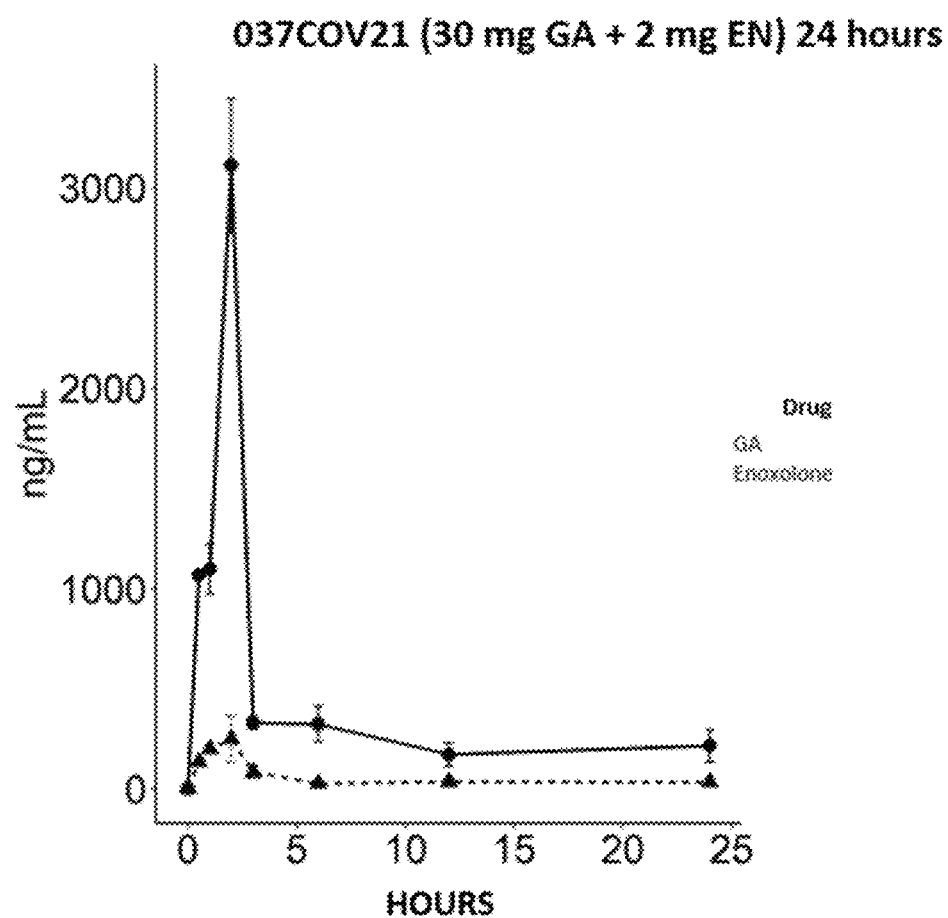
Figure 16:
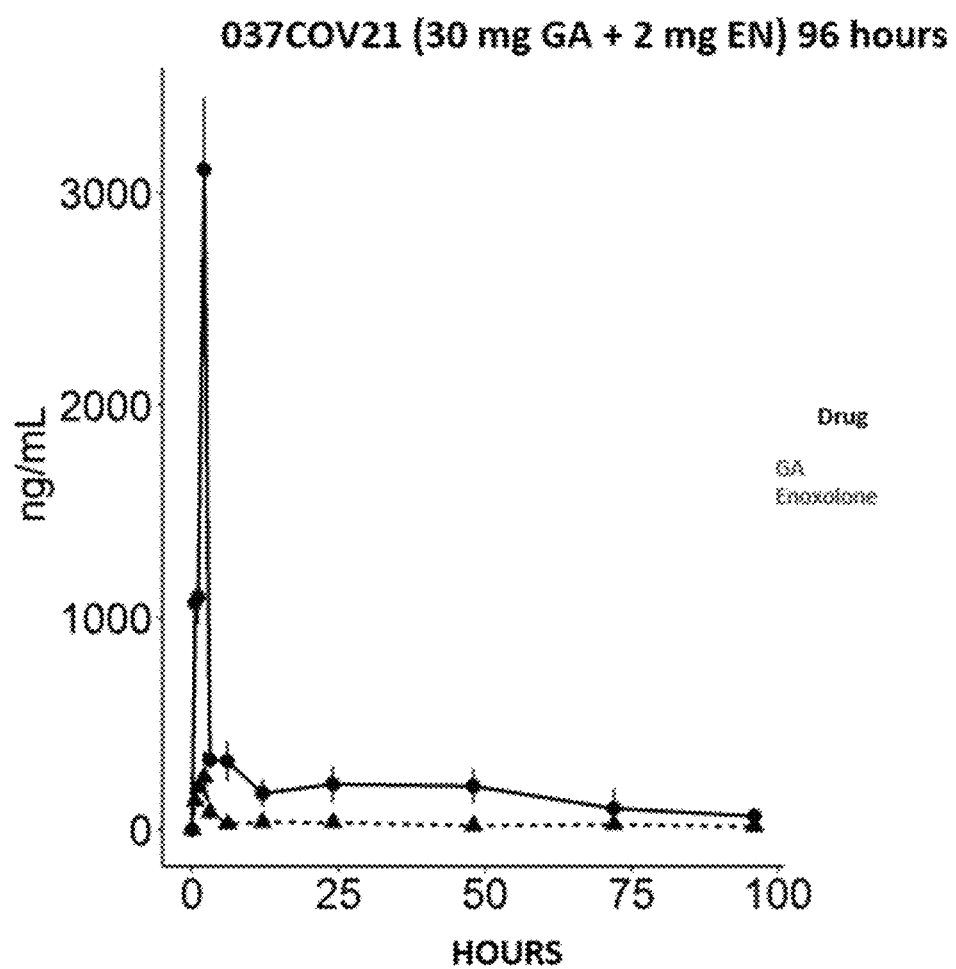

In FIGS. 15 and 16, corresponding to the 037COV21 formulation, the initial time results denote clear differences regarding the individual administration of GA and EN, wherein its administration as a mixture has effects on its absorption, distribution and metabolization, obtaining a higher $C_{max}$ compared to the 038COV21 formulation (with 60 mg GA in the absence of EN). Regarding the results obtained after 24 hours, no additional significant differences were observed.

Figure 17:
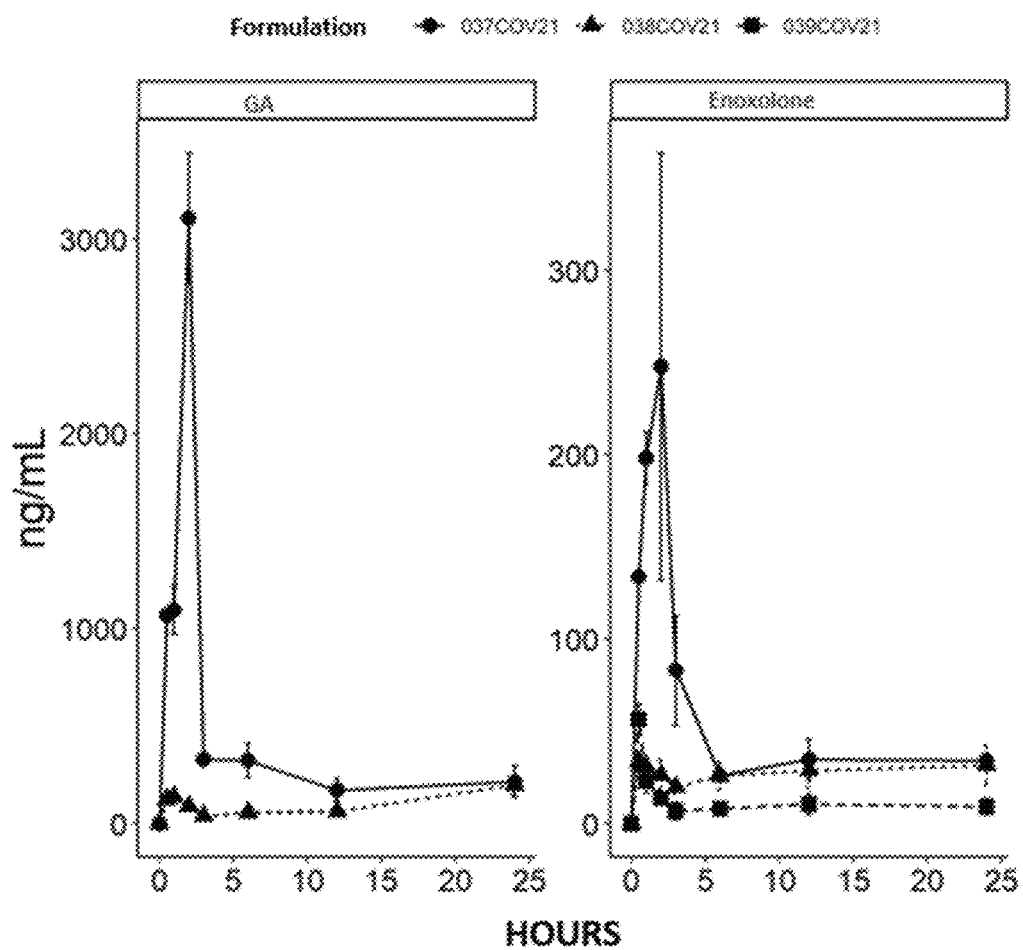
FIG. 17. Pharmacokinetic behavior graph of the GA-EN combination formulation (037COV21) against their individual administration (038COV21 and 039COV21).

Still, the absorption of EN denotes a synergistic effect obtained by the effect of the 037COV21 mixture and whose Area Under the Curve is greater than the one obtained from the 039COV21 (3 mg EN) and 038COV21 (GA metabolization) formulations (1258.47 vs 664.50 and 253.41, respectively), but being slightly higher than that of oral administration (75 mg GA). Finally, no significant differences were observed regarding the behavior of the 037COV21, 038COV21 and 039COV21 formulations after 24 hours. FIG. 17 compares the AUC of the combination formulation (037COV21) against individual drug administration (038COV21 and 039COV21). As it may be observed in the AUC values (1258.47 vs. 664.50 and 253.41 for EN) (9372.09 vs. 2297.631 for GA), the combination formulations denote a greater systemic exposure of both drugs compared to the expected exposure from their individual administration. From previous results, the administration of these drugs by inhalation focuses on the target organ, achieving similar systemic effects similar than GA administration by the oral route.

Figure 18:
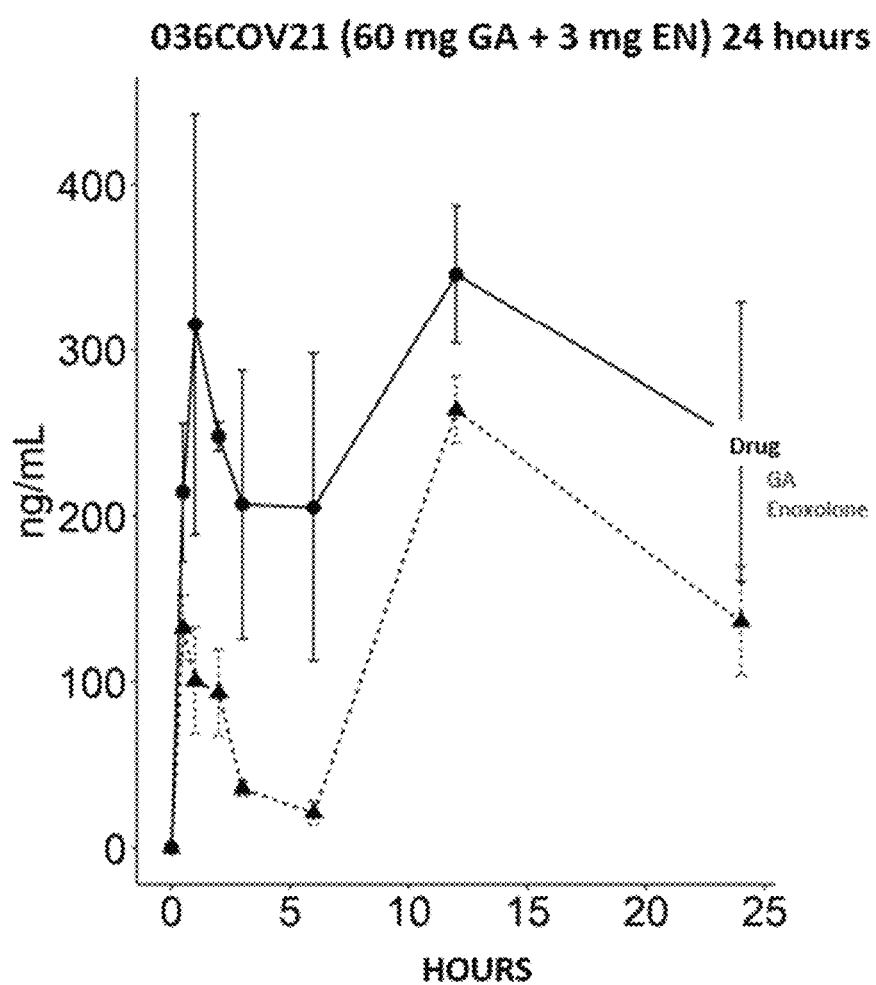
FIGS. 18 and 19. Pharmacokinetic graphs for combination of 60 mg GA and 3 mg EN (ratio 20:1) (036COV21), corresponding to 24 and 96 hours.
Figure 19:
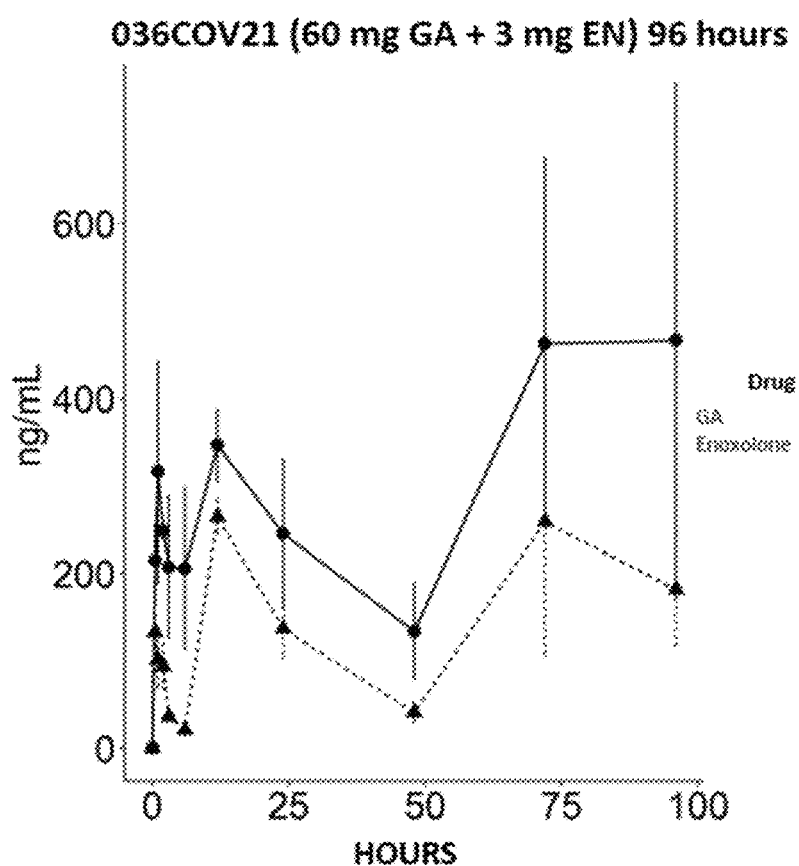
Figure 20:
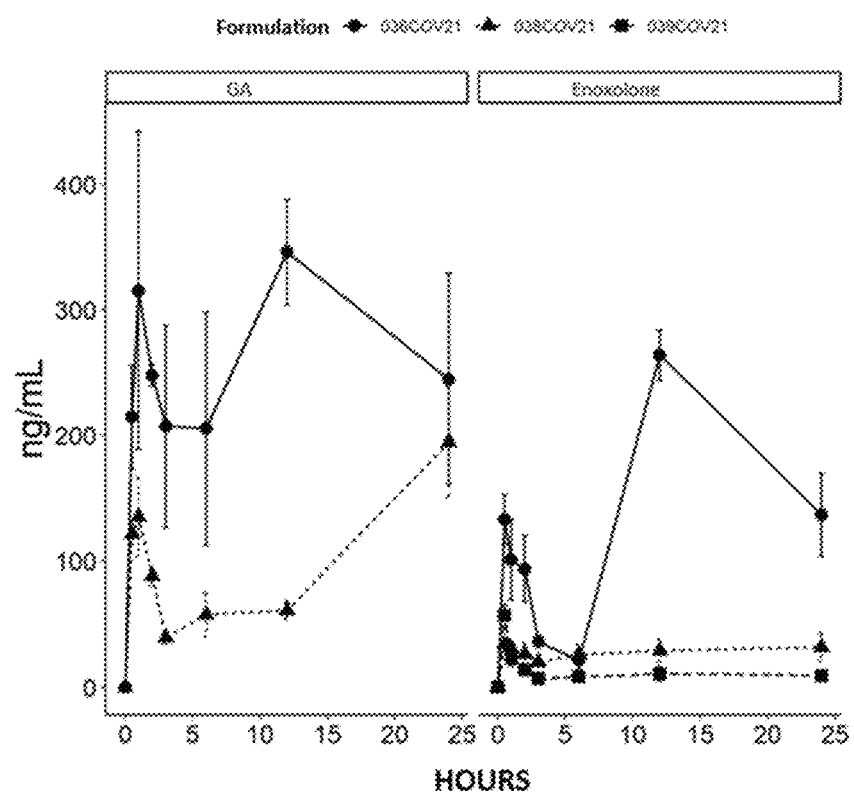
FIG. 20. Pharmacokinetic graphs of different formulations corresponding to 24 hours.
Figure 21:
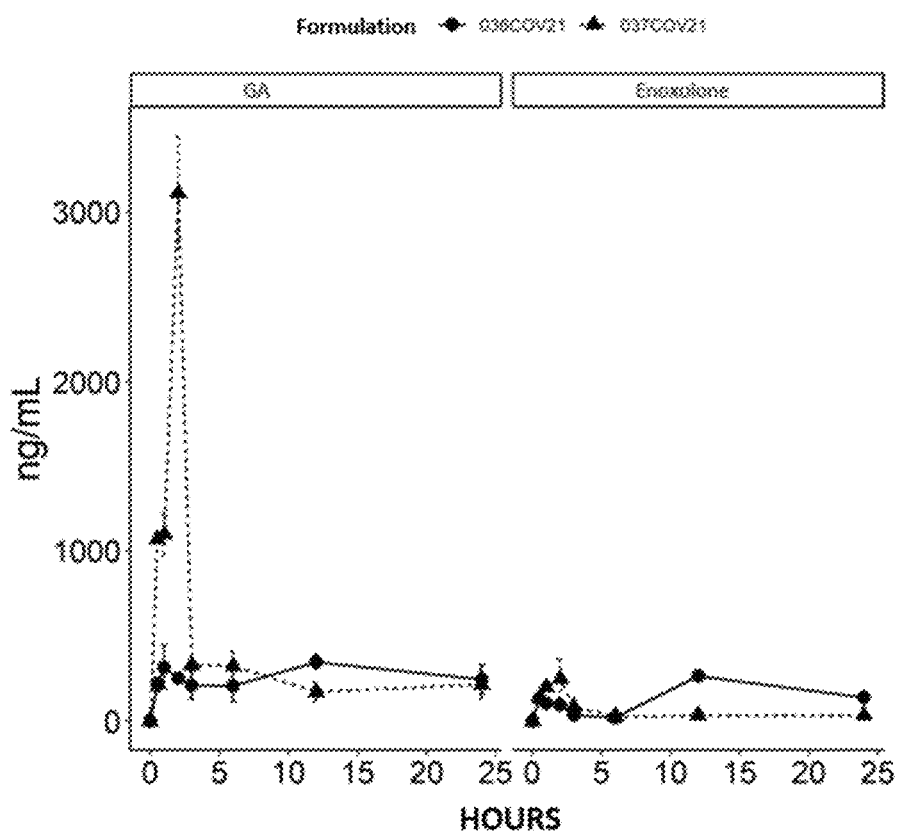
FIG. 21. Pharmacokinetic graphs of different formulations corresponding to 24 hours.

As it is observed in FIGS. 18 and 19, the formulations that include a combination of GA and EN show Area Under the Curve values higher than the values from the individual administration of these drugs. In FIG. 20, a synergistic effect can be seen when comparing these combinations against each other. Here, changes in active compound ratios (20:1 in the 036COV21 sample vs 15:1 in the 037COV21 sample) exert an impact on the behavior of the pharmacokinetic curves, specifically in their corresponding AUC. As it may be observed, for EN, 3594.57 in 036COV21 vs. 1258.47 in 037COV21, and 6510.27 in 036COV21 vs. 9372.09 in 037COV21 for GA. These changes cannot be explained only by changes in pharmacokinetic formulation concentrations since, as observed, the AUC values for the formulations are not proportional to the active compound concentrations used.

Although both formulations indicate technical advantages compared to their individual GA and EN administrations, the preference for a combined pharmaceutical form (036COV21 or 037COV21) depends on the drug to be potentiated in terms of systemic exposure. For example, if it is desired to potentiate the exposure to AG, it is preferably suggested to use the formulation 037COV21; while, if it is desired to potentiate EN exposure, it is suggested to preferably use the 036COV21 formulation.

TABLE 11

| Formulation | GA Concentration | EN Concentration | GA AUC | EN AUC |
|---|---|---|---|---|
| 036COV21 | 60 mg | 3 mg | 6510.27 | 3594.57 |
| 037COV21 | 30 mg | 2 mg | 9372.09 | 1258.47 |

This entire dataset evidences the technical advantages from GA-EN pharmaceutical formulations compared to their individual administrations. In addition to the increase in AUC for both components in the combined formulations, the results reveal that changes in their proportions modulate their systemic exposure, independently of the concentration used in the formulation. The usefulness of this modulation, and the preferred proportions and concentrations are based on the therapeutic interests for using these formulations.

ANALYSIS

The results obtained for both analytes within the 036COV21 formulation (20:1 AG-EN ratio) delimit the behavior of the modified-release pharmaceutical form, for which, two maximum values are obtained before 24 hours. This is the same effect observed in the 038COV21 formulation (GA) but obtaining higher plasma concentrations due to the previously mentioned effect of EN on GA. Regarding EN, a lower initial concentration close to 150 ng/mL is observed, but this concentration is lower than that the one obtained in the 037COV21 formulation (15:1 GA-EN ratio), an effect that limits absorption but increases residence time. That is, the therapeutic effects of EN, such as antiviral action and antimicrobial effect, can be potentiated when increasing its residence time. Furthermore, the second peak value before 24 hours evidences a plasma concentration close to 250 ng/mL, a peak value not observed in the study formulations, and which is higher than the values obtained after the oral administration of 75 mg of GA.

In addition, it is observed that EN increases its half life time and AUC with respect to the 037COV21 formulation, defining a bicompartmental absorption. In other words, the analyte is absorbed and distributed to the organs to exert its therapeutic effect or to be metabolized (liver). However, if neither retained nor metabolized, it is redirected to the circulatory system (CS) to restart its metabolism again, which extends its therapeutic effect. This effect is usually attributed to the plasma concentration of the analytes, i.e., when the plasma concentration exceeds the defined number of enzymes that promote their metabolism, the liver redirects the intact EN to the circulatory system to subsequently restart its metabolism and eventually discharge it from the body.

Hence, the proportion defined for the 036COV21 formulation conditions its absorption both by potentiating GA permeation and by limiting EN absorption.

The plasmatic concentration obtained delimits its elimination in a dose-dependent manner, which increases their residence time, thus potentiating their systemic therapeutic effects.

Having described the invention, it is claimed as property of the owner, the contents of the following claims:

1. A pharmaceutical composition that comprises a synergistic combination of at least two pentacyclic triterpenoids to be used for the treatment of viral infections, wherein
   the at least two pentacyclic triterpenoids comprise 18β-glycyrrhetinic acid and glycyrrhizinic acid; and
   a ratio of the 18β-glycyrrhetinic acid to the glycyrrhizinic acid is 1:5 to 1:25.

2. The pharmaceutical composition of claim 1 for use in treatment of viral infections, wherein the viral infection is a respiratory viral infection.

3. The pharmaceutical composition according to claim 1 further comprising at least one pharmaceutically acceptable additive.

4. The pharmaceutical composition according to claim 1, wherein the synergistic combination of 18β-glycyrrhetinic acid and glycyrrhizinic acid is in a ratio of 1:5 to 1:20.

5. The pharmaceutical composition according to claim 3, wherein the pharmaceutically acceptable additives comprise solubilizers, surfactants and solvents.

6. The pharmaceutical composition according to claim 5 wherein the solubilizers are selected from the group comprising propylene glycol, glycerin/PEG, poloxamer, polyoxylglyceride derivatives (Labrasol), glyceryl isostearate/glyceryl monostearate, glycerol derivatives, polyethylene glycol 660 12-hydroxystearate, castor oil, and the derivatives thereof.

7. The pharmaceutical composition according to claim 6, wherein the solubilizers are in a concentration of 70% to 80% m/m.

8. The pharmaceutical composition according to claim 5, wherein the surfactants are selected from the group comprising polysorbate, sorbitan monostearate, sorbitol esters, polysorbate 20,60,80.

9. The pharmaceutical composition according to claim 8, wherein the surfactants are in a concentration of 0.1% to 7% m/m.

10. The pharmaceutical composition according to claim 5, wherein the solubilizer comprises diethylene glycol monoethyl ether.

11. The pharmaceutical composition according to claim 10, wherein the solubilizer is in a concentration of 1% to 6% m/m.

12. The pharmaceutical composition according to claim 5, wherein the solvents comprise water at 10% to 20%.

13. The pharmaceutical composition according to claim 1, wherein the glycyrrhizinic acid content is from 0.1% to 20% and the 18β-glycyrrhetinic acid content is from 0.01 to 4%.

14. The pharmaceutical composition according to claim 1, wherein the content of the synergistic combination is in the range of greater than 0.0% to less than or equal to 30%.

15. The pharmaceutical composition according to claim 1, wherein the content of the synergistic combination is in the range of 0.01% to 10%.

* * * * *